(12) United States Patent
Frevert et al.

(10) Patent No.: US 9,975,929 B2
(45) Date of Patent: May 22, 2018

(54) RECOMBINANT CLOSTRIDIAL NEUROTOXINS WITH INCREASED DURATION OF EFFECT

(71) Applicant: MERZ PHARMA GmbH & CO. KGaA, Frankfurt am Main (DE)

(72) Inventors: Jürgen Frevert, Berlin (DE); Fred Hofmann, Potsdam (DE); Michael Schmidt, Potsdam (DE)

(73) Assignee: MERZ PHARMA GmbH & CO. KGaA, Frankfurt am Main (DE)

( * ) Notice: Subject to any disclaimer, the term of this patent is extended or adjusted under 35 U.S.C. 154(b) by 0 days. days.

(21) Appl. No.: 15/123,408

(22) PCT Filed: Mar. 4, 2015

(86) PCT No.: PCT/EP2015/000489
§ 371 (c)(1),
(2) Date: Sep. 2, 2016

(87) PCT Pub. No.: WO2015/132004
PCT Pub. Date: Sep. 11, 2015

(65) Prior Publication Data
US 2017/0058006 A1    Mar. 2, 2017

(30) Foreign Application Priority Data
Mar. 5, 2014 (EP) .................................. 14000791

(51) Int. Cl.
*C07K 14/33* (2006.01)
*A61K 38/00* (2006.01)

(52) U.S. Cl.
CPC ...... *C07K 14/33* (2013.01); *C12Y 304/11013* (2013.01); *A61K 38/00* (2013.01); *C07K 2319/00* (2013.01)

(58) Field of Classification Search
None
See application file for complete search history.

(56) References Cited

FOREIGN PATENT DOCUMENTS

| | | |
|---|---|---|
| WO | WO 02/08268 A2 | 1/2002 |
| WO | WO 2008/156134 A1 | 5/2002 |
| WO | WO 0240506 A2 | 5/2002 |
| WO | WO 2011/144756 A1 | 11/2011 |
| WO | WO 2013/068472 | 5/2013 |

OTHER PUBLICATIONS

Li et al. Molecular characterization of type E Clostridium botulinum and comparison to other types of Clostridium botulinum. Biochim Biophys Acta. Jan. 7, 1998;1395(1):21-7.*
Botulinum neurotoxin type E non-toxic component. https://www.ncbi.nlm.nih.gov/protein/p46082[Dec. 11, 2017] (Year: 1993).*
Lauren Cox. Botox Jabs: A New Weapon Against Chronic Pain. ABC news Jan. 17, 2008. http://abcnews.go.com/Health/PainManagement/story?id=4148566&page=1 [Dec. 10, 2017 3:18:39 PM] (Year: 2008).*
Ravichandran et al. An Initial Assessment of the Systemic Pharmacokinetics of Botulinum Toxin. JPET 318:1343-1351, 2006. (Year : 2006).*
International Search Report and Written Opinion for PCT/EP2015/000489 dated May 6, 2015.
Patrick Stancombe, et al., FEBS Journal, vol. 279, No. 3, p. 515-523, Feb. 23, 2012/.

* cited by examiner

*Primary Examiner* — Marcela M Cordero Garcia
*Assistant Examiner* — Jia-Hai Lee
(74) *Attorney, Agent, or Firm* — Hueschen and Sage

(57) ABSTRACT

This invention relates to novel recombinant clostridial neurotoxins exhibiting increased duration of effect and to methods for the manufacture of such recombinant clostridial neurotoxins. These novel recombinant clostridial neurotoxins comprise a random coil domain, and the methods comprise the steps of inserting a nucleic acid sequence coding for a random coil domain into a nucleic acid sequence coding for a parental clostridial neurotoxin and expression of the recombinant nucleic acid sequence comprising the random coil domain-coding sequence in a host cell. The invention further relates to novel recombinant single-chain precursor clostridial neurotoxins used in such methods, nucleic acid sequences encoding such recombinant single-chain precursor clostridial neurotoxins, and pharmaceutical compositions comprising the recombinant clostridial neurotoxin with increased duration of effect.

3 Claims, 4 Drawing Sheets

Figure 1:
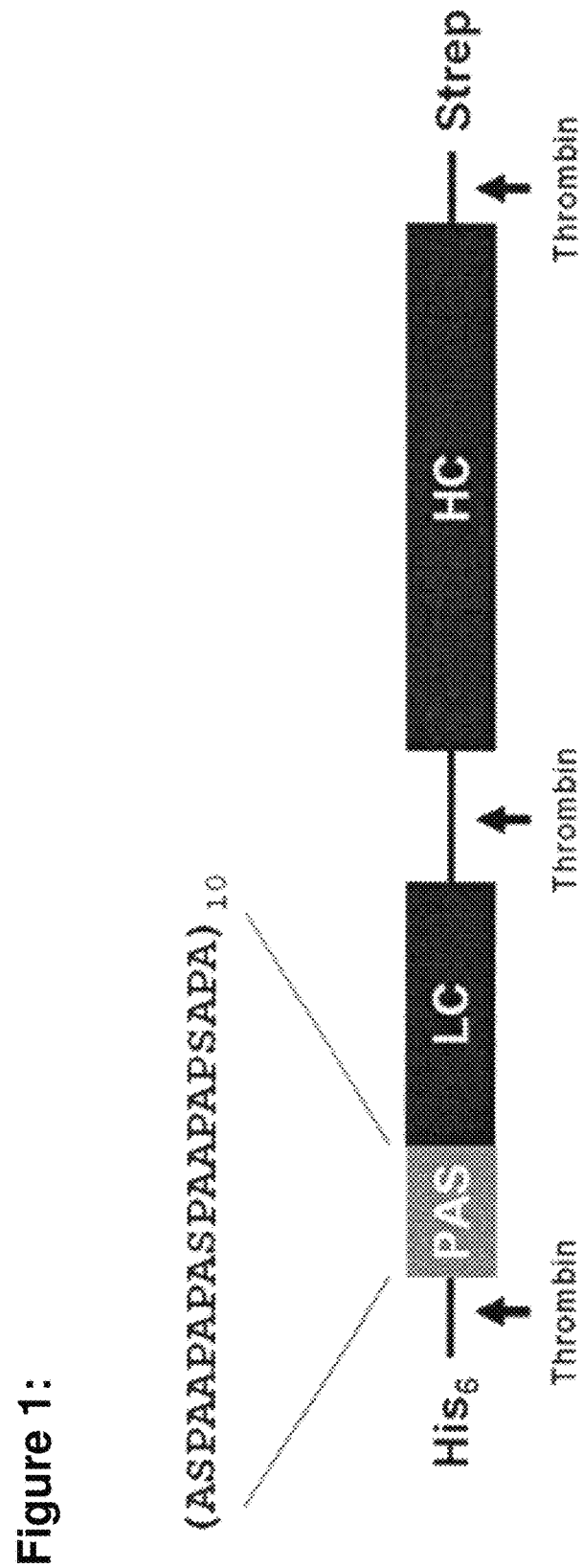

Figure 4:

[Graph showing running distance (%) vs time (d), comparing Xeomin 81208 and PAS-100-rBoNT/A]

SEQUENCE LISTING

<160> NUMBER OF SEQ ID NOS: 21

<210> SEQ ID NO 1
<211> LENGTH: 20
<212> TYPE: PRT
<213> ORGANISM: Artificial Sequence
<220> FEATURE:
<223> OTHER INFORMATION: PAS20 sequence_I

<400> SEQUENCE: 1

Ala Ser Pro Ala Ala Pro Ala Pro Ala Ser Pro Ala Ala Pro Ala Pro
1               5                   10                  15

Ser Ala Pro Ala
            20

<210> SEQ ID NO 2
<211> LENGTH: 20
<212> TYPE: PRT
<213> ORGANISM: Artificial Sequence
<220> FEATURE:
<223> OTHER INFORMATION: PAS20 sequence_II

<400> SEQUENCE: 2

Ala Ala Pro Ala Ser Pro Ala Pro Ala Ala Pro Ser Ala Pro Ala Pro
1               5                   10                  15

Ala Ala Pro Ser
            20

<210> SEQ ID NO 3
<211> LENGTH: 20
<212> TYPE: PRT
<213> ORGANISM: Artificial Sequence
<220> FEATURE:
<223> OTHER INFORMATION: PAS20 sequence_III

<400> SEQUENCE: 3

Ala Pro Ser Ser Pro Ser Pro Ser Ala Pro Ser Ser Pro Ser Pro Ala
1               5                   10                  15

Ser Pro Ser Ser
            20

<210> SEQ ID NO 4
<211> LENGTH: 20
<212> TYPE: PRT
<213> ORGANISM: Artificial Sequence
<220> FEATURE:

<223> OTHER INFORMATION: PAS20 sequence_IV

<400> SEQUENCE: 4

Ser Ala Pro Ser Ser Pro Ser Pro Ser Ala Pro Ser Ser Pro Ser Pro
1               5                   10                  15

Ala Ser Pro Ser
            20

<210> SEQ ID NO 5
<211> LENGTH: 20
<212> TYPE: PRT
<213> ORGANISM: Artificial Sequence
<220> FEATURE:
<223> OTHER INFORMATION: PAS20 sequence_V

<400> SEQUENCE: 5

Ser Ser Pro Ser Ala Pro Ser Pro Ser Ser Pro Ala Ser Pro Ser Pro
1               5                   10                  15

Ser Ser Pro Ala
            20

<210> SEQ ID NO 6
<211> LENGTH: 24
<212> TYPE: PRT
<213> ORGANISM: Artificial Sequence
<220> FEATURE:
<223> OTHER INFORMATION: PAS24 sequence_I

<400> SEQUENCE: 6

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 7
<211> LENGTH: 20
<212> TYPE: PRT
<213> ORGANISM: Artificial Sequence
<220> FEATURE:
<223> OTHER INFORMATION: PAS20 sequence_VI

<400> SEQUENCE: 7

Ala Ser Ala Ala Ala Pro Ala Ala Ala Ser Ala Ala Ala Ser Ala Pro
1               5                   10                  15

Ser Ala Ala Ala
            20

<210> SEQ ID NO 8
<211> LENGTH: 1546
<212> TYPE: PRT
<213> ORGANISM: Artificial Sequence
<220> FEATURE:
<223> OTHER INFORMATION: PAS200 rBoNT/A: protein sequence

<400> SEQUENCE: 8

Met Gly Ser Ser His His His His His His Gly Ser Leu Val Pro Arg
1               5                   10                  15

Ser Ser Ala Ser Pro Ala Ala Pro Ala Pro Ala Ser Pro Ala Ala
            20                  25                  30

Pro Ala Pro Ser Ala Pro Ala Ala Ser Pro Ala Ala Pro Ala Pro Ala
        35                  40                  45

Ser Pro Ala Ala Pro Ala Pro Ser Ala Pro Ala Ala Ser Pro Ala Ala
    50                  55                  60

-continued

Pro Ala Pro Ala Ser Pro Ala Ala Pro Ala Pro Ser Ala Pro Ala Ala
65                  70                  75                  80

Ser Pro Ala Ala Pro Ala Pro Ala Ser Pro Ala Ala Pro Ala Pro Ser
                85                  90                  95

Ala Pro Ala Ala Ser Pro Ala Ala Pro Ala Pro Ala Ser Pro Ala Ala
                100                 105                 110

Pro Ala Pro Ser Ala Pro Ala Ala Ser Pro Ala Ala Pro Ala Pro Ala
                115                 120                 125

Ser Pro Ala Ala Pro Ala Pro Ser Ala Pro Ala Ala Ser Pro Ala Ala
130                 135                 140

Pro Ala Pro Ala Ser Pro Ala Ala Pro Ala Ser Ala Pro Ala Ala
145                 150                 155                 160

Ser Pro Ala Ala Pro Ala Pro Ser Ala Pro Ala Ala Pro Ala Pro Ser
                165                 170                 175

Ala Pro Ala Ala Ser Pro Ala Ala Pro Ala Pro Ala Ser Pro Ala Ala
                180                 185                 190

Pro Ala Pro Ser Ala Pro Ala Ala Ser Pro Ala Ala Pro Ala Pro Ala
                195                 200                 205

Ser Pro Ala Ala Pro Ala Pro Ser Ala Pro Ala Ala Pro Phe Val Asn
210                 215                 220

Lys Gln Phe Asn Tyr Lys Asp Pro Val Asn Gly Val Asp Ile Ala Tyr
225                 230                 235                 240

Ile Lys Ile Pro Asn Ala Gly Gln Met Gln Pro Val Lys Ala Phe Lys
                245                 250                 255

Ile His Asn Lys Ile Trp Val Ile Pro Glu Arg Asp Thr Phe Thr Asn
                260                 265                 270

Pro Glu Glu Gly Asp Leu Asn Pro Pro Glu Ala Lys Gln Val Pro
                275                 280                 285

Val Ser Tyr Tyr Asp Ser Thr Tyr Leu Ser Thr Asp Asn Glu Lys Asp
                290                 295                 300

Asn Tyr Leu Lys Gly Val Thr Lys Leu Phe Glu Arg Ile Tyr Ser Thr
305                 310                 315                 320

Asp Leu Gly Arg Met Leu Leu Thr Ser Ile Val Arg Gly Ile Pro Phe
                325                 330                 335

Trp Gly Gly Ser Thr Ile Asp Thr Glu Leu Lys Val Ile Asp Thr Asn
                340                 345                 350

Cys Ile Asn Val Ile Gln Pro Asp Gly Ser Tyr Arg Ser Glu Glu Leu
                355                 360                 365

Asn Leu Val Ile Ile Gly Pro Ser Ala Asp Ile Ile Gln Phe Glu Cys
                370                 375                 380

Lys Ser Phe Gly His Glu Val Leu Asn Leu Thr Arg Asn Gly Tyr Gly
385                 390                 395                 400

Ser Thr Gln Tyr Ile Arg Phe Ser Pro Asp Phe Thr Phe Gly Phe Glu
                405                 410                 415

Glu Ser Leu Glu Val Asp Thr Asn Pro Leu Leu Gly Ala Gly Lys Phe
                420                 425                 430

Ala Thr Asp Pro Ala Val Thr Leu Ala His Glu Leu Ile His Ala Gly
                435                 440                 445

His Arg Leu Tyr Gly Ile Ala Ile Asn Pro Asn Arg Val Phe Lys Val
                450                 455                 460

Asn Thr Asn Ala Tyr Tyr Glu Met Ser Gly Leu Glu Val Ser Phe Glu
465                 470                 475                 480

-continued

Glu Leu Arg Thr Phe Gly Gly His Asp Ala Lys Phe Ile Asp Ser Leu
            485                 490                 495

Gln Glu Asn Glu Phe Arg Leu Tyr Tyr Asn Lys Phe Lys Asp Ile
        500                 505                 510

Ala Ser Thr Leu Asn Lys Ala Lys Ser Ile Val Gly Thr Thr Ala Ser
            515                 520                 525

Leu Gln Tyr Met Lys Asn Val Phe Lys Glu Lys Tyr Leu Leu Ser Glu
        530                 535                 540

Asp Thr Ser Gly Lys Phe Ser Val Asp Lys Leu Lys Phe Asp Lys Leu
545                 550                 555                 560

Tyr Lys Met Leu Thr Glu Ile Tyr Thr Glu Asp Asn Phe Val Lys Phe
            565                 570                 575

Phe Lys Val Leu Asn Arg Lys Thr Tyr Leu Asn Phe Asp Lys Ala Val
        580                 585                 590

Phe Lys Ile Asn Ile Val Pro Lys Val Asn Tyr Thr Ile Tyr Asp Gly
        595                 600                 605

Phe Asn Leu Arg Asn Thr Asn Leu Ala Ala Asn Phe Asn Gly Gln Asn
        610                 615                 620

Thr Glu Ile Asn Asn Met Asn Phe Thr Lys Leu Lys Asn Phe Thr Gly
625                 630                 635                 640

Leu Phe Glu Phe Tyr Lys Leu Leu Cys Val Arg Gly Ile Ile Thr Ser
            645                 650                 655

Lys Ala Gly Ala Gly Lys Ser Leu Val Pro Arg Gly Ser Ala Gly Ala
            660                 665                 670

Gly Ala Leu Asn Asp Leu Cys Ile Lys Val Asn Asn Trp Asp Leu Phe
        675                 680                 685

Phe Ser Pro Ser Glu Asp Asn Phe Thr Asn Asp Leu Asn Lys Gly Glu
        690                 695                 700

Glu Ile Thr Ser Asp Thr Asn Ile Glu Ala Ala Glu Glu Asn Ile Ser
705                 710                 715                 720

Leu Asp Leu Ile Gln Gln Tyr Tyr Leu Thr Phe Asn Phe Asp Asn Glu
            725                 730                 735

Pro Glu Asn Ile Ser Ile Glu Asn Leu Ser Ser Asp Ile Ile Gly Gln
        740                 745                 750

Leu Glu Leu Met Pro Asn Ile Glu Arg Phe Pro Asn Gly Lys Lys Tyr
        755                 760                 765

Glu Leu Asp Lys Tyr Thr Met Phe His Tyr Leu Arg Ala Gln Glu Phe
        770                 775                 780

Glu His Gly Lys Ser Arg Ile Ala Leu Thr Asn Ser Val Asn Glu Ala
785                 790                 795                 800

Leu Leu Asn Pro Ser Arg Val Tyr Thr Phe Phe Ser Ser Asp Tyr Val
            805                 810                 815

Lys Lys Val Asn Lys Ala Thr Glu Ala Ala Met Phe Leu Gly Trp Val
        820                 825                 830

Glu Gln Leu Val Tyr Asp Phe Thr Asp Glu Thr Ser Glu Val Ser Thr
        835                 840                 845

Thr Asp Lys Ile Ala Asp Ile Thr Ile Ile Pro Tyr Ile Gly Pro
850                 855                 860

Ala Leu Asn Ile Gly Asn Met Leu Tyr Lys Asp Asp Phe Val Gly Ala
865                 870                 875                 880

Leu Ile Phe Ser Gly Ala Val Ile Leu Leu Glu Phe Ile Pro Glu Ile
            885                 890                 895

Ala Ile Pro Val Leu Gly Thr Phe Ala Leu Val Ser Tyr Ile Ala Asn

```
                900             905             910
Lys Val Leu Thr Val Gln Thr Ile Asp Asn Ala Leu Ser Lys Arg Asn
            915                 920                 925

Glu Lys Trp Asp Glu Val Tyr Lys Tyr Ile Val Thr Asn Trp Leu Ala
        930                 935                 940

Lys Val Asn Thr Gln Ile Asp Leu Ile Arg Lys Lys Met Lys Glu Ala
945                 950                 955                 960

Leu Glu Asn Gln Ala Glu Ala Thr Lys Ala Ile Ile Asn Tyr Gln Tyr
                965                 970                 975

Asn Gln Tyr Thr Glu Glu Lys Asn Asn Ile Asn Phe Asn Ile Asp
            980                 985                 990

Asp Leu Ser Ser Lys Leu Asn Glu  Ser Ile Asn Lys Ala  Met Ile Asn
        995                 1000                1005

Ile Asn  Lys Phe Leu Asn Gln  Cys Ser Val Ser Tyr  Leu Met Asn
        1010                1015                1020

Ser Met  Ile Pro Tyr Gly Val  Lys Arg Leu Glu Asp  Phe Asp Ala
        1025                1030                1035

Ser Leu  Lys Asp Ala Leu Leu  Lys Tyr Ile Tyr Asp  Asn Arg Gly
        1040                1045                1050

Thr Leu  Ile Gly Gln Val Asp  Arg Leu Lys Asp Lys  Val Asn Asn
        1055                1060                1065

Thr Leu  Ser Thr Asp Ile Pro  Phe Gln Leu Ser Lys  Tyr Val Asp
        1070                1075                1080

Asn Gln  Arg Leu Leu Ser Thr  Phe Thr Glu Tyr Ile  Lys Asn Ile
        1085                1090                1095

Ile Asn  Thr Ser Ile Leu Asn  Leu Arg Tyr Glu Ser  Asn His Leu
        1100                1105                1110

Ile Asp  Leu Ser Arg Tyr Ala  Ser Lys Ile Asn Ile  Gly Ser Lys
        1115                1120                1125

Val Asn  Phe Asp Pro Ile Asp  Lys Asn Gln Ile Gln  Leu Phe Asn
        1130                1135                1140

Leu Glu  Ser Ser Lys Ile Glu  Val Ile Leu Lys Asn  Ala Ile Val
        1145                1150                1155

Tyr Asn  Ser Met Tyr Glu Asn  Phe Ser Thr Ser Phe  Trp Ile Arg
        1160                1165                1170

Ile Pro  Lys Tyr Phe Asn Ser  Ile Ser Leu Asn Asn  Glu Tyr Thr
        1175                1180                1185

Ile Ile  Asn Cys Met Glu Asn  Asn Ser Gly Trp Lys  Val Ser Leu
        1190                1195                1200

Asn Tyr  Gly Glu Ile Ile Trp  Thr Leu Gln Asp Thr  Gln Glu Ile
        1205                1210                1215

Lys Gln  Arg Val Val Phe Lys  Tyr Ser Gln Met Ile  Asn Ile Ser
        1220                1225                1230

Asp Tyr  Ile Asn Arg Trp Ile  Phe Val Thr Ile Thr  Asn Asn Arg
        1235                1240                1245

Leu Asn  Asn Ser Lys Ile Tyr  Ile Asn Gly Arg Leu  Ile Asp Gln
        1250                1255                1260

Lys Pro  Ile Ser Asn Leu Gly  Asn Ile His Ala Ser  Asn Asn Ile
        1265                1270                1275

Met Phe  Lys Leu Asp Gly Cys  Arg Asp Thr His Arg  Tyr Ile Trp
        1280                1285                1290

Ile Lys  Tyr Phe Asn Leu Phe  Asp Lys Glu Leu Asn  Glu Lys Glu
        1295                1300                1305
```

```
Ile Lys Asp Leu Tyr Asp Asn Gln Ser Asn Ser Gly Ile Leu Lys
1310                1315                1320

Asp Phe Trp Gly Asp Tyr Leu Gln Tyr Asp Lys Pro Tyr Tyr Met
1325                1330                1335

Leu Asn Leu Tyr Asp Pro Asn Lys Tyr Val Asp Val Asn Asn Val
1340                1345                1350

Gly Ile Arg Gly Tyr Met Tyr Leu Lys Gly Pro Arg Gly Ser Val
1355                1360                1365

Met Thr Thr Asn Ile Tyr Leu Asn Ser Ser Leu Tyr Arg Gly Thr
1370                1375                1380

Lys Phe Ile Ile Lys Tyr Ala Ser Gly Asn Lys Asp Asn Ile
1385                1390                1395

Val Arg Asn Asn Asp Arg Val Tyr Ile Asn Val Val Lys Asn
1400                1405                1410

Lys Glu Tyr Arg Leu Ala Thr Asn Ala Ser Gln Ala Gly Val Glu
1415                1420                1425

Lys Ile Leu Ser Ala Leu Glu Ile Pro Asp Val Gly Asn Leu Ser
1430                1435                1440

Gln Val Val Val Met Lys Ser Lys Asn Asp Gln Gly Ile Thr Asn
1445                1450                1455

Lys Cys Lys Met Asn Leu Gln Asp Asn Asn Gly Asn Asp Ile Gly
1460                1465                1470

Phe Ile Gly Phe His Gln Phe Asn Asn Ile Ala Lys Leu Val Ala
1475                1480                1485

Ser Asn Trp Tyr Asn Arg Gln Ile Glu Arg Ser Ser Arg Thr Leu
1490                1495                1500

Gly Cys Ser Trp Glu Phe Ile Pro Val Asp Asp Gly Trp Gly Glu
1505                1510                1515

Arg Pro Leu Gly Asp Leu Val Pro Arg Gly Ser Ala Asn Ser Ser
1520                1525                1530

Ser Val Asp Lys Leu Trp Ser His Pro Gln Phe Glu Lys
1535                1540                1545

<210> SEQ ID NO 9
<211> LENGTH: 1446
<212> TYPE: PRT
<213> ORGANISM: Artificial Sequence
<220> FEATURE:
<223> OTHER INFORMATION: PAS100 rBoNT/A: protein sequence

<400> SEQUENCE: 9

Met Gly Ser Ser His His His His His His Gly Ser Leu Val Pro Arg
1               5                   10                  15

Ser Ser Ser Ala Ser Pro Ala Ala Pro Ala Pro Ala Ser Pro Ala Ala
                20                  25                  30

Pro Ala Pro Ser Ala Pro Ala Ala Ser Pro Ala Ala Pro Ala Pro Ala
            35                  40                  45

Ser Pro Ala Ala Pro Ala Pro Ser Ala Pro Ala Ala Ser Pro Ala Ala
        50                  55                  60

Pro Ala Pro Ala Ser Pro Ala Ala Pro Ala Pro Ser Ala Pro Ala Ala
65                  70                  75                  80

Ser Pro Ala Ala Pro Ala Pro Ala Ser Pro Ala Ala Pro Ala Pro Ser
                85                  90                  95

Ala Pro Ala Ala Ser Pro Ala Ala Pro Ala Pro Ala Ser Pro Ala Ala
            100                 105                 110
```

```
Pro Ala Pro Ser Ala Pro Ala Ala Pro Phe Val Asn Lys Gln Phe Asn
            115                 120                 125

Tyr Lys Asp Pro Val Asn Gly Val Asp Ile Ala Tyr Ile Lys Ile Pro
130                 135                 140

Asn Ala Gly Gln Met Gln Pro Val Lys Ala Phe Lys Ile His Asn Lys
145                 150                 155                 160

Ile Trp Val Ile Pro Glu Arg Asp Thr Phe Thr Asn Pro Glu Glu Gly
                165                 170                 175

Asp Leu Asn Pro Pro Glu Ala Lys Gln Val Pro Val Ser Tyr Tyr
            180                 185                 190

Asp Ser Thr Tyr Leu Ser Thr Asp Asn Glu Lys Asp Asn Tyr Leu Lys
            195                 200                 205

Gly Val Thr Lys Leu Phe Glu Arg Ile Tyr Ser Thr Asp Leu Gly Arg
        210                 215                 220

Met Leu Leu Thr Ser Ile Val Arg Gly Ile Pro Phe Trp Gly Gly Ser
225                 230                 235                 240

Thr Ile Asp Thr Glu Leu Lys Val Ile Asp Thr Asn Cys Ile Asn Val
                245                 250                 255

Ile Gln Pro Asp Gly Ser Tyr Arg Ser Glu Glu Leu Asn Leu Val Ile
            260                 265                 270

Ile Gly Pro Ser Ala Asp Ile Ile Gln Phe Glu Cys Lys Ser Phe Gly
        275                 280                 285

His Glu Val Leu Asn Leu Thr Arg Asn Gly Tyr Gly Ser Thr Gln Tyr
        290                 295                 300

Ile Arg Phe Ser Pro Asp Phe Thr Phe Gly Phe Glu Glu Ser Leu Glu
305                 310                 315                 320

Val Asp Thr Asn Pro Leu Leu Gly Ala Gly Lys Phe Ala Thr Asp Pro
                325                 330                 335

Ala Val Thr Leu Ala His Glu Leu Ile His Ala Gly His Arg Leu Tyr
            340                 345                 350

Gly Ile Ala Ile Asn Pro Asn Arg Val Phe Lys Val Asn Thr Asn Ala
        355                 360                 365

Tyr Tyr Glu Met Ser Gly Leu Glu Val Ser Phe Glu Glu Leu Arg Thr
    370                 375                 380

Phe Gly Gly His Asp Ala Lys Phe Ile Asp Ser Leu Gln Glu Asn Glu
385                 390                 395                 400

Phe Arg Leu Tyr Tyr Tyr Asn Lys Phe Lys Asp Ile Ala Ser Thr Leu
                405                 410                 415

Asn Lys Ala Lys Ser Ile Val Gly Thr Thr Ala Ser Leu Gln Tyr Met
            420                 425                 430

Lys Asn Val Phe Lys Glu Lys Tyr Leu Leu Ser Glu Asp Thr Ser Gly
        435                 440                 445

Lys Phe Ser Val Asp Lys Leu Lys Phe Asp Lys Leu Tyr Lys Met Leu
    450                 455                 460

Thr Glu Ile Tyr Thr Glu Asp Asn Phe Val Lys Phe Phe Lys Val Leu
465                 470                 475                 480

Asn Arg Lys Thr Tyr Leu Asn Phe Asp Lys Ala Val Phe Lys Ile Asn
                485                 490                 495

Ile Val Pro Lys Val Asn Tyr Thr Ile Tyr Asp Gly Phe Asn Leu Arg
            500                 505                 510

Asn Thr Asn Leu Ala Ala Asn Phe Asn Gly Gln Asn Thr Glu Ile Asn
        515                 520                 525
```

-continued

```
Asn Met Asn Phe Thr Lys Leu Lys Asn Phe Thr Gly Leu Phe Glu Phe
    530                 535                 540

Tyr Lys Leu Leu Cys Val Arg Gly Ile Ile Thr Ser Lys Ala Gly Ala
545                 550                 555                 560

Gly Lys Ser Leu Val Pro Arg Gly Ser Ala Gly Ala Gly Ala Leu Asn
                565                 570                 575

Asp Leu Cys Ile Lys Val Asn Asn Trp Asp Leu Phe Phe Ser Pro Ser
                580                 585                 590

Glu Asp Asn Phe Thr Asn Asp Leu Asn Lys Gly Glu Glu Ile Thr Ser
            595                 600                 605

Asp Thr Asn Ile Glu Ala Ala Glu Glu Asn Ile Ser Leu Asp Leu Ile
610                 615                 620

Gln Gln Tyr Tyr Leu Thr Phe Asn Phe Asp Asn Glu Pro Glu Asn Ile
625                 630                 635                 640

Ser Ile Glu Asn Leu Ser Ser Asp Ile Ile Gly Gln Leu Glu Leu Met
                645                 650                 655

Pro Asn Ile Glu Arg Phe Pro Asn Gly Lys Lys Tyr Glu Leu Asp Lys
                660                 665                 670

Tyr Thr Met Phe His Tyr Leu Arg Ala Gln Glu Phe Glu His Gly Lys
            675                 680                 685

Ser Arg Ile Ala Leu Thr Asn Ser Val Asn Glu Ala Leu Leu Asn Pro
690                 695                 700

Ser Arg Val Tyr Thr Phe Ser Ser Asp Tyr Val Lys Lys Val Asn
705                 710                 715                 720

Lys Ala Thr Glu Ala Ala Met Phe Leu Gly Trp Val Glu Gln Leu Val
                725                 730                 735

Tyr Asp Phe Thr Asp Glu Thr Ser Glu Val Ser Thr Thr Asp Lys Ile
                740                 745                 750

Ala Asp Ile Thr Ile Ile Ile Pro Tyr Ile Gly Pro Ala Leu Asn Ile
            755                 760                 765

Gly Asn Met Leu Tyr Lys Asp Asp Phe Val Gly Ala Leu Ile Phe Ser
770                 775                 780

Gly Ala Val Ile Leu Leu Glu Phe Ile Pro Glu Ile Ala Ile Pro Val
785                 790                 795                 800

Leu Gly Thr Phe Ala Leu Val Ser Tyr Ile Ala Asn Lys Val Leu Thr
                805                 810                 815

Val Gln Thr Ile Asp Asn Ala Leu Ser Lys Arg Asn Glu Lys Trp Asp
                820                 825                 830

Glu Val Tyr Lys Tyr Ile Val Thr Asn Trp Leu Ala Lys Val Asn Thr
            835                 840                 845

Gln Ile Asp Leu Ile Arg Lys Lys Met Lys Glu Ala Leu Glu Asn Gln
850                 855                 860

Ala Glu Ala Thr Lys Ala Ile Ile Asn Tyr Gln Tyr Asn Gln Tyr Thr
865                 870                 875                 880

Glu Glu Glu Lys Asn Asn Ile Asn Phe Asn Ile Asp Asp Leu Ser Ser
                885                 890                 895

Lys Leu Asn Glu Ser Ile Asn Lys Ala Met Ile Asn Ile Asn Lys Phe
                900                 905                 910

Leu Asn Gln Cys Ser Val Ser Tyr Leu Met Asn Ser Met Ile Pro Tyr
            915                 920                 925

Gly Val Lys Arg Leu Glu Asp Phe Asp Ala Ser Leu Lys Asp Ala Leu
930                 935                 940

Leu Lys Tyr Ile Tyr Asp Asn Arg Gly Thr Leu Ile Gly Gln Val Asp
```

```
                945                 950                 955                 960
            Arg Leu Lys Asp Lys Val Asn Thr Leu Ser Thr Asp Ile Pro Phe
                            965                 970                 975
            Gln Leu Ser Lys Tyr Val Asp Asn Gln Arg Leu Leu Ser Thr Phe Thr
                                980                 985                 990
            Glu Tyr Ile Lys Asn Ile Ile Asn Thr Ser Ile Leu Asn Leu Arg Tyr
                        995                 1000                1005
            Glu Ser Asn His Leu Ile Asp Leu Ser Arg Tyr Ala Ser Lys Ile
                1010                1015                1020
            Asn Ile Gly Ser Lys Val Asn Phe Asp Pro Ile Asp Lys Asn Gln
                1025                1030                1035
            Ile Gln Leu Phe Asn Leu Glu Ser Ser Lys Ile Glu Val Ile Leu
                1040                1045                1050
            Lys Asn Ala Ile Val Tyr Asn Ser Met Tyr Glu Asn Phe Ser Thr
                1055                1060                1065
            Ser Phe Trp Ile Arg Ile Pro Lys Tyr Phe Asn Ser Ile Ser Leu
                1070                1075                1080
            Asn Asn Glu Tyr Thr Ile Ile Asn Cys Met Glu Asn Asn Ser Gly
                1085                1090                1095
            Trp Lys Val Ser Leu Asn Tyr Gly Glu Ile Ile Trp Thr Leu Gln
                1100                1105                1110
            Asp Thr Gln Glu Ile Lys Gln Arg Val Val Phe Lys Tyr Ser Gln
                1115                1120                1125
            Met Ile Asn Ile Ser Asp Tyr Ile Asn Arg Trp Ile Phe Val Thr
                1130                1135                1140
            Ile Thr Asn Asn Arg Leu Asn Asn Ser Lys Ile Tyr Ile Asn Gly
                1145                1150                1155
            Arg Leu Ile Asp Gln Lys Pro Ile Ser Asn Leu Gly Asn Ile His
                1160                1165                1170
            Ala Ser Asn Asn Ile Met Phe Lys Leu Asp Gly Cys Arg Asp Thr
                1175                1180                1185
            His Arg Tyr Ile Trp Ile Lys Tyr Phe Asn Leu Phe Asp Lys Glu
                1190                1195                1200
            Leu Asn Glu Lys Glu Ile Lys Asp Leu Tyr Asp Asn Gln Ser Asn
                1205                1210                1215
            Ser Gly Ile Leu Lys Asp Phe Trp Gly Asp Tyr Leu Gln Tyr Asp
                1220                1225                1230
            Lys Pro Tyr Tyr Met Leu Asn Leu Tyr Asp Pro Asn Lys Tyr Val
                1235                1240                1245
            Asp Val Asn Asn Val Gly Ile Arg Gly Tyr Met Tyr Leu Lys Gly
                1250                1255                1260
            Pro Arg Gly Ser Val Met Thr Thr Asn Ile Tyr Leu Asn Ser Ser
                1265                1270                1275
            Leu Tyr Arg Gly Thr Lys Phe Ile Ile Lys Lys Tyr Ala Ser Gly
                1280                1285                1290
            Asn Lys Asp Asn Ile Val Arg Asn Asn Asp Arg Val Tyr Ile Asn
                1295                1300                1305
            Val Val Val Lys Asn Lys Glu Tyr Arg Leu Ala Thr Asn Ala Ser
                1310                1315                1320
            Gln Ala Gly Val Glu Lys Ile Leu Ser Ala Leu Glu Ile Pro Asp
                1325                1330                1335
            Val Gly Asn Leu Ser Gln Val Val Val Met Lys Ser Lys Asn Asp
                1340                1345                1350
```

| Gln | Gly | Ile | Thr | Asn | Lys | Cys | Lys | Met | Asn | Leu | Gln | Asp | Asn | Asn |
|-----|-----|-----|-----|-----|-----|-----|-----|-----|-----|-----|-----|-----|-----|-----|
|     | 1355|     |     |     | 1360|     |     |     |     | 1365|     |     |     |     |

| Gly | Asn | Asp | Ile | Gly | Phe | Ile | Gly | Phe | His | Gln | Phe | Asn | Asn | Ile |
|-----|-----|-----|-----|-----|-----|-----|-----|-----|-----|-----|-----|-----|-----|-----|
|     | 1370|     |     |     |     | 1375|     |     |     |     | 1380|     |     |     |

| Ala | Lys | Leu | Val | Ala | Ser | Asn | Trp | Tyr | Asn | Arg | Gln | Ile | Glu | Arg |
|-----|-----|-----|-----|-----|-----|-----|-----|-----|-----|-----|-----|-----|-----|-----|
|     | 1385|     |     |     |     | 1390|     |     |     |     | 1395|     |     |     |

| Ser | Ser | Arg | Thr | Leu | Gly | Cys | Ser | Trp | Glu | Phe | Ile | Pro | Val | Asp |
|-----|-----|-----|-----|-----|-----|-----|-----|-----|-----|-----|-----|-----|-----|-----|
|     | 1400|     |     |     |     | 1405|     |     |     |     | 1410|     |     |     |

| Asp | Gly | Trp | Gly | Glu | Arg | Pro | Leu | Gly | Asp | Leu | Val | Pro | Arg | Gly |
|-----|-----|-----|-----|-----|-----|-----|-----|-----|-----|-----|-----|-----|-----|-----|
|     | 1415|     |     |     |     | 1420|     |     |     |     | 1425|     |     |     |

| Ser | Ala | Asn | Ser | Ser | Ser | Val | Asp | Lys | Leu | Trp | Ser | His | Pro | Gln |
|-----|-----|-----|-----|-----|-----|-----|-----|-----|-----|-----|-----|-----|-----|-----|
|     | 1430|     |     |     |     | 1435|     |     |     |     | 1440|     |     |     |

| Phe | Glu | Lys |
|-----|-----|-----|
|     | 1445|     |

<210> SEQ ID NO 10
<211> LENGTH: 4641
<212> TYPE: DNA
<213> ORGANISM: Artificial Sequence
<220> FEATURE:
<223> OTHER INFORMATION: PAS200 rBoNT/A: DNA sequence

<400> SEQUENCE: 10

```
atgggcagca gccatcatca tcaccatcat ggtagcctgg ttccgcgtag ctcttctgca      60
agtccggcag caccggcacc ggcttcacca gctgcaccag cacctagcgc accggcagca     120
tctccagcag cccctgcacc ggcaagccct gcagctccag caccgtcagc accagcagca     180
agcccagctg ctcctgctcc agcgagccca gcagcgccag ctcctagtgc cctgctgcc      240
tctcctgctg ctccggcacc agcaagtcct gctgcgcctg caccgagtgc tccggctgct     300
agtcctgccg caccagctcc ggctagtcca gctgctccag ccccttcagc tccggcagct     360
tcccctgcag cgcctgcccc tgccagtcca gcggctcctg cacctagtgc gcctgcagct     420
tcaccggctg cccctgcgcc agcttctcct gcggctccag ctccatctgc cccagccgca     480
tccccagcgg caccagctcc agcttctccg gcagcgccag caccttctgc gcctgccgca     540
tctcctgcag caccagcgcc tgcgagtcct gcagctcctg ctccttcagc cctgcggca      600
agtccagcag caccagcccc agcaagccca gccgcaccag caccatctgc ccctgcagca     660
ccatttgtga caagcagtt taactataag acccggtga acggtgtgga tatcgcgtat      720
atcaaaatcc cgaatgcggg ccagatgcaa ccagtcaagg cgttcaagat tcataacaag     780
atttgggtta ttccggaacg tgataccttc accaatccgg aagaaggcga cttaaacccg     840
ccgccagaag ccaaacaagt gccggtgagc tactatgata gcacgtatct tagcaccgat     900
aatgaaaaag acaattacct gaagggcgtg accaagttgt tcgagcgcat ctacagtacc     960
gacttaggcc gcatgttgtt gacgagcatc gttcgcggta tcccgttctg gggcggctcg    1020
accattgata ccgagttgaa agtcattgac acgaactgta tcaatgttat ccaaccggac    1080
ggcagttatc gcagcgagga gttaaatttg gtcatcatcg gtccaagcgc agatattatt    1140
cagttcgaat gcaagagctt cggccatgag tcttgaatt tgacgcgcaa cggttacggc    1200
agcacccaat acatccgctt tagcccggat ttcacctttg cttcgagga gagcttggag    1260
gtggacacca acccgctgtt aggtgccggc aaattcgcaa ccgacccggc agtgacgttg    1320
gcgcacgaat tgattcatgc gggtcaccgc ttatacggta tcgcgatcaa tccgaatcgc    1380
gtctttaaag tcaataccaa cgcgtactac gaaatgagcg gcttagaggt tagctttgaa    1440
```

```
gaattacgca ccttcggtgg ccacgacgcc aagttcatcg acagcctgca ggaaaatgag    1500
ttccgcttgt actattacaa taaattcaag gacatcgcga gcaccttaaa taaagcaaag    1560
agcattgtgg gcaccaccgc aagcttgcag tacatgaaga acgtatttaa ggaaaaatat    1620
ttgttgtcgg aggataccag cgggaaattc agcgtcgata agctgaaatt cgacaaattg    1680
tataaaatgc tgaccgagat ttacaccgag gataacttcg tcaagttttt taaggtgtta    1740
aatcgtaaga cctatttaaa ctttgataaa gcggtgttta aaattaatat cgtgccgaag    1800
gtgaattaca ccatctacga tggtttcaat ttacgcaaca cgaatctggc ggcgaatttt    1860
aatggccaaa acaccgaaat taacaacatg aactttacga agttaaagaa tttcacgggc    1920
ttattcgaat tctacaagtt attatgcgtg cgcggcatca ttaccagcaa ggcaggtgcg    1980
ggcaagtcct tggttccgcg tggcagcgcc ggcgccggcg cgctcaatga tctgtgtatt    2040
aaagtcaata actgggacct gttcttcagc ccgagcgagg ataactttac caacgactta    2100
aacaaaggcg aggagatcac gagcgatacg aacatcgagg cggcggagga aaatattagc    2160
ctggacctca ttcagcagta ctatctgacg ttcaattttg acaatgagcc ggagaacatc    2220
agcattgaaa atctcagcag cgacatcatc ggtcagttgg aactgatgcc gaacattgaa    2280
cgctttccga acggcaaaaa atatgaactg acaagtata  ccatgttcca ttacttacgc    2340
gcacaggaat ttgagcacgg caagagccgc attgcgctga ccaatagcgt taacgaggcc    2400
ttgttaaatc cgagccgtgt ctacacgttc ttcagcagcg attatgtcaa aaaagtgaac    2460
aaggcgaccg aagccgcgat gttttttggc tgggtcgagc aattggttta cgattttacc    2520
gacgaaacca gcgaggtgag cacgaccgac aaaattgcag atatcaccat catcattccg    2580
tacatcggtc cggcgctcaa tatcggcaat atgttataca aggacgactt tgtgggcgcg    2640 ctgatctttta gcggcgcggt tatcttatta gaattcatcc cggagatcgc aatcccggtc    2700
ttgggcacct ttgcgttggt gagctatatc gcgaataaag tgctcacggt ccaaaccatc    2760
gataacgcgc tcagcaagcg taatgagaaa tgggacgagg tttataagta tatcgtgacc    2820
aactggttag caaaagtcaa tacgcagatc gatctcatcc gcaaaaaaat gaaagaagcc    2880
ttggaaaatc aagcggaggc aaccaaagcc atcattaatt accagtataa ccaatatacc    2940
gaagaagaaa aaaacaatat caacttcaat atcgatgatt tgagcagcaa actgaacgag    3000
agcattaaca aagcgatgat taacatcaac aagttcttga atcaatgcag cgtgagctat    3060
ctcatgaaca gcatgatccc gtatggcgtc aaacgcttgg aagattttga cgccagcctg    3120
aaagatgcgc tcctcaagta tatttatgac aaccgcggca ccctcattgg ccaggtggac    3180
cgcttgaagg ataaagtgaa caatacgctc agcacggata tcccgttcca gctgagcaag    3240
tacgtcgaca accagcgctt actgagcacc tttaccgagt atatcaagaa catcattaat    3300
accagcatcc tcaacttgcg ctatgagagc aatcacctga tcgacctcag ccgctacgcc    3360
agcaagatca acatcggcag caaggtcaat ttcgacccga tcgataagaa tcagatccaa    3420
ttgtttaacc tggaaagcag caagatcgag gttatcttga agaacgcgat tgtgtacaac    3480
agcatgtacg agaactttag cacgagcttc tggattcgta tcccgaagta tttcaatagc    3540
attagcctga ataacgaata taccattatc aactgcatgg aaaataatag cggctggaag    3600
gtgagcttaa attacggcga gatcatttgg accttacagg ataccccaaga aatcaaacag    3660 cgcgtcgtct ttaagtatag ccagatgatc aacatcagcg attacatcaa ccgctggatc    3720
ttcgtgacca tcaccaataa tcgcttgaat aatagcaaga tttacatcaa tggtcgcttg    3780
```

| | |
|---|---|
| attgatcaaa aaccgatcag caatctcggt aatatccatg ccagcaataa catcatgttt | 3840 |
| aagttagacg gttgccgcga tacccaccgc tatatctgga tcaagtattt taacttattt | 3900 |
| gataaggaac tcaacgaaaa ggaaattaaa gacttatatg acaatcagag caatagcggc | 3960 |
| atcctgaagg atttctgggg cgactacctg cagtacgata gccgtacta tatgttgaac | 4020 |
| ttgtatgacc cgaacaaata tgtcgatgtg aacaatgtgg gtattcgtgg ctatatgtac | 4080 |
| ttaaagggcc cgcgtggtag cgtgatgacc acgaatattt acttaaacag cagcttatac | 4140 |
| cgcggcacga agtttattat caagaagtat gccagcggca acaaggacaa tatcgtccgc | 4200 |
| aacaacgacc gtgtgtatat taacgtggtg gtgaagaata aagagtaccg cttggccacg | 4260 |
| aatgcgagcc aggcgggcgt ggaaaaaatc ttgagcgcgt tggagatccc ggacgtcggc | 4320 |
| aacctcagcc aggttgtggt gatgaagtct aaaaacgacc agggcatcac gaacaagtgc | 4380 |
| aaaatgaatt tgcaagataa caacggcaac gacatcggct ttattggttt tcaccagttc | 4440 |
| aataacatcg ccaaactcgt ggccagcaat tggtataacc gccaaattga acgcagcagc | 4500 |
| cgcacgctcg gctgtagctg ggagttcatc ccggtgacga tggctgggg cgagcgcccg | 4560 |
| ctcggagatc tggtgccacg cggttccgcg aattcgagct ccgtcgacaa gctttggagc | 4620 |
| cacccgcagt tcgaaaaata a | 4641 |

<210> SEQ ID NO 11
<211> LENGTH: 4341
<212> TYPE: DNA
<213> ORGANISM: Artificial Sequence
<220> FEATURE:
<223> OTHER INFORMATION: PAS100 rBoNT/A: DNA sequence

<400> SEQUENCE: 11

| | |
|---|---|
| atgggtagca gccatcatca tcaccatcat ggtagcctgg ttccgcgtag ctcttctgca | 60 |
| agtccggcag caccggcacc ggcttcacca gctgcaccag cacctagcgc accggcagca | 120 |
| tctccagcag cccctgcacc ggcaagccct gcagctccag caccgtcagc accagcagca | 180 |
| agcccagctg ctcctgctcc agcgagccca gcagcgccag ctcctagtgc ccctgctgcc | 240 |
| tctcctgctg ctccggcacc agcaagtcct gctgcgcctg caccgagtgc tccggctgct | 300 |
| agtcctgccg caccagctcc ggctagtcca gctgctccag ccccttcagc ccctgcagca | 360 |
| ccatttgtga caagcagtt taactataag gacccggtga acggtgtgga tatcgcgtat | 420 |
| atcaaaatcc cgaatgcggg ccagatgcaa ccagtcaagg cgttcaagat tcataacaag | 480 |
| atttgggtta ttccggaacg tgataccttc accaatccgg aagaaggcga tttaaatccg | 540 |
| ccgccagaag ccaaacaagt gccggtgagc tactatgata gcacgtatct tagcaccgat | 600 |
| aatgaaaaag acaattacct gaagggcgtg accaagttgt tcgagcgcat ctacagtacc | 660 |
| gacttaggcc gcatgttgtt gacgagcatc gttcgcggta tcccgttctg gggcggctcg | 720 |
| accattgata ccgagttgaa agtcattgac acgaactgta tcaatgttat ccaaccggac | 780 |
| ggcagttatc gcagcgagga gttaaatttg gtcatcatcg gtccaagcgc agatattatt | 840 |
| cagttcgaat gcaagagctt cggccatgag gtcttgaatt tgacgcgcaa cggttacggc | 900 |
| agcacccaat acatccgctt tagcccggat ttcacctttg gcttcgagga gagcttggag | 960 |
| gtggacacca accgctgtt aggtgccggc aaattcgcaa ccgaccggc agtgacgttg | 1020 |
| gcgcacgaat tgattcatgc gggtcaccgc ttatacggta tcgcgatcaa tccgaatcgc | 1080 |
| gtctttaaag tcaataccaa cgcgtactac gaaatgagcg gcttagaggt tagctttgaa | 1140 |
| gaattacgca ccttcggtgg ccacgacgcc aagttcatcg acagcctgca ggaaaatgag | 1200 |

```
ttccgcttgt actattacaa taaattcaag gacatcgcga gcaccttaaa taaagcaaag   1260
agcattgtgg gcaccaccgc aagcttgcag tacatgaaga acgtatttaa ggaaaaatat   1320
ttgttgtcgg aggataccag cgggaaattc agcgtcgata agctgaaatt cgacaaattg   1380
tataaaatgc tgaccgagat ttacaccgag gataacttcg tcaagttttt taaggtgtta   1440
aatcgtaaga cctatttaaa ctttgataaa gcggtgttta aaattaatat cgtgccgaag   1500
gtgaattaca ccatctacga tggtttcaat ttacgcaaca cgaatctggc ggcgaatttt   1560
aatggccaaa acaccgaaat taacaacatg aactttacga agttaaagaa tttcacgggc   1620
ttattcgaat tctacaagtt attatgcgtg cgcggcatca ttaccagcaa ggcaggtgcg   1680
ggcaagtcct tggttccgcg tggcagcgcc ggcgccggcg cgctcaatga tctgtgtatt   1740
aaagtcaata actgggacct gttcttcagc ccgagcgagg ataactttac caacgactta   1800
aacaaaggcg aggagatcac gagcgatacg aacatcgagg cggcggagga aatattagc    1860 ctggacctca ttcagcagta ctatctgacg ttcaattttg acaatgagcc ggagaacatc   1920
agcattgaaa atctcagcag cgacatcatc ggtcagttgg aactgatgcc gaacattgaa   1980
cgctttccga acggcaaaaa atatgaactg gacaagtata ccatgttcca ttacttacgc   2040
gcacaggaat ttgagcacgg caagagccgc attgcgctga ccaatagcgt taacgaggcc   2100
ttgttaaatc cgagccgtgt ctacacgttc ttcagcagcg attatgtcaa aaaagtgaac   2160
aaggcgaccg aagccgcgat gttttgggc tgggtcgagc aattggttta cgattttacc    2220
gacgaaacca gcgaggtgag cacgaccgac aaaattgcag atatcaccat catcattccg   2280
tacatcggtc cggcgctcaa tatcggcaat atgttataca aggacgactt tgtgggcgcg   2340
ctgatcttta gcggcgcggt tatcttatta gaattcatcc cggagatcgc aatcccggtc   2400
ttgggcacct ttgcgttggt gagctatatc gcgaataaag tgctcacggt ccaaaccatc   2460
gataacgcgc tcagcaagcg taatgagaaa tgggacgagg tttataagta tatcgtgacc   2520
aactggttag caaaagtcaa tacgcagatc gatctcatcc gcaaaaaaat gaaagaagcc   2580
ttggaaaatc aagcggaggc aaccaaagcc atcattaatt accagtataa ccaatatacc   2640
gaagaagaaa aaaacaatat caacttcaat atcgatgatt tgagcagcaa actgaacgag   2700
agcattaaca aagcgatgat taacatcaac aagttcttga atcaatgcag cgtgagctat   2760
ctcatgaaca gcatgatccc gtatggcgtc aaacgcttgg aagattttga cgccagcctg   2820
aaagatgcgc tcctcaagta tatttatgac aaccgcggca ccctcattgg ccaggtggac   2880
cgcttgaagg ataaagtgaa caatacgctc agcacggata tcccgttcca gctgagcaag   2940
tacgtcgaca accagcgctt actgagcacc tttaccgagt atatcaagaa catcattaat   3000
accagcatcc tcaacttgcg ctatgagagc aatcacctga tcgacctcag ccgctacgcc   3060
agcaagatca acatcggcag caaggtcaat ttcgacccga tcgataagaa tcagatccaa   3120
ttgtttaacc tggaaagcag caagatcgag gttatcttga agaacgcgat tgtgtacaac   3180
agcatgtacg agaactttag cacgagcttc tggattcgta tcccgaagta tttcaatagc   3240
attagcctga ataacgaata taccattatc aactgcatgg aaaataatag cggctggaag   3300
gtgagcttaa attcggcga gatcatttgg accttacagg ataccaaga atcaaacag      3360 cgcgtcgtct ttaagtatag ccagatgatc aacatcagcg attacatcaa ccgctggatc   3420
ttcgtgacca tcaccaataa tcgcttgaat aatagcaaga tttacatcaa tggtcgcttg   3480
attgatcaaa aaccgatcag caatctcggt aatatccatg ccagcaataa catcatgttt   3540
```

```
aagttagacg gttgccgcga tacccaccgc tatatctgga tcaagtattt taacttattt    3600
gataaggaac tcaacgaaaa ggaaattaaa gacttatatg acaatcagag caatagcggc    3660
atcctgaagg atttctgggg cgactacctg cagtacgata agccgtacta tatgttgaac    3720
ttgtatgacc cgaacaaata tgtcgatgtg aacaatgtgg gtattcgtgg ctatatgtac    3780
ttaaagggcc cgcgtggtag cgtgatgacc acgaatattt acttaaacag cagcttatac    3840
cgcggcacga gtttattat caagaagtat gccagcggca acaaggacaa tatcgtccgc     3900
aacaacgacc gtgtgtatat taacgtggtg gtgaagaata aagagtaccg cttggccacg    3960
aatgcgagcc aggcgggcgt ggaaaaaatc ttgagcgcgt tggagatccc ggacgtcggc    4020
aacctcagcc aggttgtggt gatgaagtct aaaaacgacc agggcatcac gaacaagtgc    4080
aaaatgaatt tgcaagataa caacggcaac gacatcggct ttattggttt tcaccagttc    4140
aataacatcg ccaaactcgt ggccagcaat tggtataacc gccaaattga acgcagcagc    4200
cgcacgctcg gctgtagctg ggagttcatc ccggtggacg atggctgggg cgagcgcccg    4260
ctcggagatc tggtgccacg cggttccgcg aattcgagct ccgtcgacaa gctttggagc    4320
cacccgcagt tcgaaaaata a                                              4341
```

<210> SEQ ID NO 12
<211> LENGTH: 20
<212> TYPE: PRT
<213> ORGANISM: Artificial Sequence
<220> FEATURE:
<223> OTHER INFORMATION: PAS60 to PAS500: (ASPAAPAPASPAAPAPSAPA)n, with
      n being an integer selected from 3 to 25
<220> FEATURE:
<221> NAME/KEY: REPEAT
<222> LOCATION: (1)..(20)
<223> OTHER INFORMATION: (ASPAAPAPASPAAPAPSAPA)n, with n being an
      integer selected from 3 to 25

<400> SEQUENCE: 12

Ala Ser Pro Ala Ala Pro Ala Pro Ala Ser Pro Ala Ala Pro Ala Pro
1               5                   10                  15

Ser Ala Pro Ala
            20

<210> SEQ ID NO 13
<211> LENGTH: 20
<212> TYPE: PRT
<213> ORGANISM: Artificial Sequence
<220> FEATURE:
<223> OTHER INFORMATION: PAS80 to PAS160: (ASPAAPAPASPAAPAPSAPA)n, with
      n being an integer selected from 4 to 8
<220> FEATURE:
<221> NAME/KEY: REPEAT
<222> LOCATION: (1)..(20)
<223> OTHER INFORMATION: (ASPAAPAPASPAAPAPSAPA)n, with n being an
      integer selected from 4 to 8

<400> SEQUENCE: 13

Ala Ser Pro Ala Ala Pro Ala Pro Ala Ser Pro Ala Ala Pro Ala Pro
1               5                   10                  15

Ser Ala Pro Ala
            20

<210> SEQ ID NO 14
<211> LENGTH: 20
<212> TYPE: PRT
<213> ORGANISM: Artificial Sequence
<220> FEATURE:
<223> OTHER INFORMATION: PAS100 to PAS200: (ASPAAPAPASPAAPAPSAPA)n, with -continued n being an integer selected from 5 to 10
<220> FEATURE:
<221> NAME/KEY: REPEAT
<222> LOCATION: (1)..(20)
<223> OTHER INFORMATION: (ASPAAPAPASPAAPAPSAPA)n, with n being an
      integer selected from 5 to 10

<400> SEQUENCE: 14

Ala Ser Pro Ala Ala Pro Ala Pro Ala Ser Pro Ala Ala Pro Ala Pro
1               5                   10                  15

Ser Ala Pro Ala
            20

<210> SEQ ID NO 15
<211> LENGTH: 100
<212> TYPE: PRT
<213> ORGANISM: Artificial Sequence
<220> FEATURE:
<223> OTHER INFORMATION: PAS100: (ASPAAPAPASPAAPAPSAPA)n, with n being 5

<400> SEQUENCE: 15

Ala Ser Pro Ala Ala Pro Ala Pro Ala Ser Pro Ala Ala Pro Ala Pro
1               5                   10                  15

Ser Ala Pro Ala Ala Ser Pro Ala Ala Pro Ala Pro Ala Ser Pro Ala
            20                  25                  30

Ala Pro Ala Pro Ser Ala Pro Ala Ala Ser Pro Ala Ala Pro Ala Pro
        35                  40                  45

Ala Ser Pro Ala Ala Pro Ala Pro Ser Ala Pro Ala Ala Ser Pro Ala
    50                  55                  60

Ala Pro Ala Pro Ala Ser Pro Ala Ala Pro Ala Pro Ser Ala Pro Ala
65                  70                  75                  80

Ala Ser Pro Ala Ala Pro Ala Pro Ala Ser Pro Ala Ala Pro Ala Pro
            85                  90                  95

Ser Ala Pro Ala
            100

<210> SEQ ID NO 16
<211> LENGTH: 200
<212> TYPE: PRT
<213> ORGANISM: Artificial Sequence
<220> FEATURE:
<223> OTHER INFORMATION: PAS200: (ASPAAPAPASPAAPAPSAPA)n, with n being
      10

<400> SEQUENCE: 16

Ala Ser Pro Ala Ala Pro Ala Pro Ala Ser Pro Ala Ala Pro Ala Pro
1               5                   10                  15

Ser Ala Pro Ala Ala Ser Pro Ala Ala Pro Ala Pro Ala Ser Pro Ala
            20                  25                  30

Ala Pro Ala Pro Ser Ala Pro Ala Ala Ser Pro Ala Ala Pro Ala Pro
        35                  40                  45

Ala Ser Pro Ala Ala Pro Ala Pro Ser Ala Pro Ala Ala Ser Pro Ala
    50                  55                  60

Ala Pro Ala Pro Ala Ser Pro Ala Ala Pro Ala Pro Ser Ala Pro Ala
65                  70                  75                  80

Ala Ser Pro Ala Ala Pro Ala Pro Ala Ser Pro Ala Ala Pro Ala Pro
            85                  90                  95

Ser Ala Pro Ala Ala Ser Pro Ala Ala Pro Ala Pro Ala Ser Pro Ala
            100                 105                 110

Ala Pro Ala Pro Ser Ala Pro Ala Ala Ser Pro Ala Ala Pro Ala Pro

```
                115                 120                 125
Ala Ser Pro Ala Ala Pro Ala Pro Ser Ala Pro Ala Ala Ser Pro Ala
            130                 135                 140

Ala Pro Ala Pro Ala Ser Pro Ala Ala Pro Ala Pro Ser Ala Pro Ala
145                 150                 155                 160

Ala Ser Pro Ala Ala Pro Ala Pro Ala Ser Pro Ala Ala Pro Ala Pro
                165                 170                 175

Ser Ala Pro Ala Ala Ser Pro Ala Ala Pro Ala Pro Ala Ser Pro Ala
            180                 185                 190

Ala Pro Ala Pro Ser Ala Pro Ala
        195                 200

<210> SEQ ID NO 17
<211> LENGTH: 20
<212> TYPE: PRT
<213> ORGANISM: Artificial Sequence
<220> FEATURE:
<223> OTHER INFORMATION: PAS100 to PAS3000: (ASPAAPAPASPAAPAPSAPA)n,
      with n being an integer selected from 5 to 150
<220> FEATURE:
<221> NAME/KEY: REPEAT
<222> LOCATION: (1)..(20)
<223> OTHER INFORMATION: (ASPAAPAPASPAAPAPSAPA)n, with n being an
      integer selected from 5 to 150

<400> SEQUENCE: 17

Ala Ser Pro Ala Ala Pro Ala Pro Ala Ser Pro Ala Ala Pro Ala Pro
1               5                   10                  15

Ser Ala Pro Ala
            20

<210> SEQ ID NO 18
<211> LENGTH: 20
<212> TYPE: PRT
<213> ORGANISM: Artificial Sequence
<220> FEATURE:
<223> OTHER INFORMATION: PAS120 to PAS400: (ASPAAPAPASPAAPAPSAPA)n, with
      n being an integer selected from 6 to 20
<220> FEATURE:
<221> NAME/KEY: REPEAT
<222> LOCATION: (1)..(20)
<223> OTHER INFORMATION: (ASPAAPAPASPAAPAPSAPA)n, with n being an
      integer selected from 6 to 20

<400> SEQUENCE: 18

Ala Ser Pro Ala Ala Pro Ala Pro Ala Ser Pro Ala Ala Pro Ala Pro
1               5                   10                  15

Ser Ala Pro Ala
            20

<210> SEQ ID NO 19
<211> LENGTH: 20
<212> TYPE: PRT
<213> ORGANISM: Artificial Sequence
<220> FEATURE:
<223> OTHER INFORMATION: PAS140 to PAS260: (ASPAAPAPASPAAPAPSAPA)n, with
      n being an integer selected from 7 to 13
<220> FEATURE:
<221> NAME/KEY: REPEAT
<222> LOCATION: (1)..(20)
<223> OTHER INFORMATION: (ASPAAPAPASPAAPAPSAPA)n, with n being an
      integer selected from 7 to 13

<400> SEQUENCE: 19

Ala Ser Pro Ala Ala Pro Ala Pro Ala Ser Pro Ala Ala Pro Ala Pro
1               5                   10                  15
```

```
Ser Ala Pro Ala
            20

<210> SEQ ID NO 20
<211> LENGTH: 20
<212> TYPE: PRT
<213> ORGANISM: Artificial Sequence
<220> FEATURE:
<223> OTHER INFORMATION: PAS160 to PAS240: (ASPAAPAPASPAAPAPSAPA)n, with
      n being an integer selected from 8 to 12
<220> FEATURE:
<221> NAME/KEY: REPEAT
<222> LOCATION: (1)..(20)
<223> OTHER INFORMATION: (ASPAAPAPASPAAPAPSAPA)n, with n being an
      integer selected from 8 to 12

<400> SEQUENCE: 20

Ala Ser Pro Ala Ala Pro Ala Pro Ala Ser Pro Ala Ala Pro Ala Pro
1               5                   10                  15

Ser Ala Pro Ala
            20

<210> SEQ ID NO 21
<211> LENGTH: 20
<212> TYPE: PRT
<213> ORGANISM: Artificial Sequence
<220> FEATURE:
<223> OTHER INFORMATION: PAS180 to PAS220: (ASPAAPAPASPAAPAPSAPA)n, with
      n being an integer selected from 9 to 11
<220> FEATURE:
<221> NAME/KEY: REPEAT
<222> LOCATION: (1)..(20)
<223> OTHER INFORMATION: (ASPAAPAPASPAAPAPSAPA)n, with n being an
      integer selected from 9 to 11

<400> SEQUENCE: 21

Ala Ser Pro Ala Ala Pro Ala Pro Ala Ser Pro Ala Ala Pro Ala Pro
1               5                   10                  15

Ser Ala Pro Ala
            20
```

RECOMBINANT CLOSTRIDIAL NEUROTOXINS WITH INCREASED DURATION OF EFFECT

FIELD OF THE INVENTION

This invention relates to novel recombinant clostridial neurotoxins exhibiting increased duration of effect and to methods for the manufacture of such recombinant clostridial neurotoxins. These novel recombinant clostridial neurotoxins comprise a random coil domain, and the methods comprise the steps of inserting a nucleic acid sequence coding for a random coil domain into a nucleic acid sequence coding for a parental clostridial neurotoxin and expression of the recombinant nucleic acid sequence comprising the random coil domain-coding sequence in a host cell. The invention further relates to novel recombinant single-chain precursor clostridial neurotoxins used in such methods, nucleic acid sequences encoding such recombinant single-chain precursor clostridial neurotoxins, and pharmaceutical compositions comprising the recombinant clostridial neurotoxin with increased duration of effect.

BACKGROUND OF THE INVENTION

*Clostridium* is a genus of anaerobe gram-positive bacteria, belonging to the Firmicutes. *Clostridium* consists of around 100 species that include common free-living bacteria as well as important pathogens, such as *Clostridium botulinum* and *Clostridium tetani*. Both species produce neurotoxins, botulinum toxin and tetanus toxin, respectively. These neurotoxins are potent inhibitors of calcium-dependent neurotransmitter secretion of neuronal cells and are among the strongest toxins known to man. The lethal dose in humans lies between 0.1 ng and 1 ng per kilogram of body weight.

Oral ingestion of botulinum toxin via contaminated food or generation of botulinum toxin in wounds can cause botulism, which is characterized by paralysis of various muscles. Paralysis of the breathing muscles can cause death of the affected individual.

Although both botulinum neurotoxin (BoNT) and tetanus neurotoxin (TxNT) function via a similar initial physiological mechanism of action, inhibiting neurotransmitter release from the axon of the affected neuron into the synapse, they differ in their clinical response. While the botulinum toxin acts at the neuromuscular junction and other cholinergic synapses in the peripheral nervous system, inhibiting the release of the neurotransmitter acetylcholine and thereby causing flaccid paralysis, the tetanus toxin acts mainly in the central nervous system, preventing the release of the inhibitory neurotransmitters GABA (gamma-aminobutyric acid) and glycine by degrading the protein synaptobrevin. The consequent overactivity in the muscles results in generalized contractions of the agonist and antagonist musculature, termed a tetanic spasm (rigid paralysis).

While the tetanus neurotoxin exists in one immunologically distinct type, the botulinum neurotoxins are known to occur in seven different immunogenic types, termed BoNT/A through BoNT/H. Most *Clostridium botulinum* strains produce one type of neurotoxin, but strains producing multiple toxins have also been described.

Botulinum and tetanus neurotoxins have highly homologous amino acid sequences and show a similar domain structure. Their biologically active form comprises two peptide chains, a light chain of about 50 kDa and a heavy chain of about 100 kDa, linked by a disulfide bond. A linker or loop region, whose length varies among different clostridial toxins, is located between the two cysteine residues forming the disulfide bond. This loop region is proteolytically cleaved by an unknown clostridial endoprotease to obtain the biologically active toxin.

The molecular mechanism of intoxication by TxNT and BoNT appears to be similar as well: entry into the target neuron is mediated by binding of the C-terminal part of the heavy chain to a specific cell surface receptor; the toxin is then taken up by receptor-mediated endocytosis. The low pH in the so formed endosome then triggers a conformational change in the clostridial toxin which allows it to embed itself in the endosomal membrane and to translocate through the endosomal membrane into the cytoplasm, where the disulfide bond joining the heavy and the light chain is reduced. The light chain can then selectively cleave so called SNARE-proteins, which are essential for different steps of neurotransmitter release into the synaptic cleft, e.g. recognition, docking and fusion of neurotransmitter-containing vesicles with the plasma membrane. TxNT, BoNT/B, BoNT/D, BoNT/F, and BoNT/G cause proteolytic cleavage of synaptobrevin or VAMP (vesicle-associated membrane protein), BoNT/A and BoNT/E cleave the plasma membrane-associated protein SNAP-25, and BoNT/C cleaves the integral plasma membrane protein syntaxin and SNAP-25.

Clostridial neurotoxins display variable durations of action that are serotype specific. The clinical therapeutic effect of BoNT/A lasts approximately 3 months for neuromuscular disorders and 6 to 12 months for hyperhidrosis. The effects of BoNT/E, on the other hand, last less than 4 weeks. The longer lasting therapeutic effect of BoNT/A makes it preferable for clinical use compared to the other serotypes, for example serotypes B, $C_1$, D, E, F, G and H. One possible explanation for the divergent durations of action might be the distinct subcellular localizations of BoNT serotypes. The protease domain of BoNT/A light chain localizes in a punctate manner to the plasma membrane of neuronal cells, co-localizing with its substrate SNAP-25. In contrast, the short-duration BoNT/E serotype is cytoplasmic. Membrane association might protect BoNT/A from cytosolic degradation mechanisms allowing for prolonged persistence of BoNT/A in the neuronal cell.

In *Clostridium botulinum*, the botulinum toxin is formed as a protein complex comprising the neurotoxic component and non-toxic proteins. The accessory proteins embed the neurotoxic component thereby protecting it from degradation by digestive enzymes in the gastrointestinal tract. Thus, botulinum neurotoxins of most serotypes are orally toxic. Complexes with, for example, 450 kDa or with 900 kDa are obtainable from cultures of *Clostridium botulinum*.

In recent years, botulinum neurotoxins have been used as therapeutic agents in the treatment of dystonias and spasms. Preparations comprising botulinum toxin complexes are commercially available, e.g. from Ipsen Ltd (Dysport®) or Allergan Inc. (Botox®). A high purity neurotoxic component, free of any complexing proteins, is for example available from Merz Pharmaceuticals GmbH, Frankfurt (Xeomin®).

Clostridial neurotoxins are usually injected into the affected muscle tissue, bringing the agent close to the neuromuscular end plate, i.e. close to the cellular receptor mediating its uptake into the nerve cell controlling said affected muscle. Various degrees of neurotoxin spread have been observed. The neurotoxin spread is thought to depend on the injected amount and the particular neurotoxin preparation. It can result in adverse side effects such as paralysis in nearby muscle tissue, which can largely be avoided by reducing the injected doses to the therapeutically relevant level. Overdosing can also trigger the immune system to generate neutralizing antibodies that inactivate the neurotoxin preventing it from relieving the involuntary muscle activity. Immunologic tolerance to botulinum toxin has been shown to correlate with cumulative doses.

At present, clostridial neurotoxins are still predominantly produced by fermentation processes using appropriate *Clostridium* strains. However, industrial production of clostridial neurotoxin from anaerobic *Clostridium* culture is a cumbersome and time-consuming process. Due to the high toxicity of the final product, the procedure must be performed under strict containment. During the fermentation process, the single-chain precursors are proteolytically cleaved by an unknown clostridial protease to obtain the biologically active di-chain clostridial neurotoxin. The degree of neurotoxin activation by proteolytic cleavage varies between different strains and neurotoxin serotypes, which is a major consideration for the manufacture due to the requirement of neurotoxin preparations with a well-defined biological activity. Furthermore, during fermentation processes using *Clostridium* strains the clostridial neurotoxins are produced as protein complexes, in which the neurotoxic component is embedded by accessory proteins. These accessory proteins have no beneficial effect on biological activity or duration of effect. They can however trigger an immune reaction in the patient, resulting in immunity against the clostridial neurotoxin. Manufacture of recombinant clostridial neurotoxins, which are not embedded by auxiliary proteins, might therefore be advantageous.

Methods for the recombinant expression of clostridial neurotoxins in *E. coli* are well known in the art (see, for example, WO 00/12728, WO 01/14570, or WO 2006/076902). Furthermore, clostridial neurotoxins have been expressed in eukaryotic expression systems, such as in *Pichia pastoris, Pichia methanolica, Saccharomyces cerevisiae*, insect cells and mammalian cells (see WO 2006/017749).

Recombinant clostridial neurotoxins may be expressed as single-chain precursors, which subsequently have to be proteolytically cleaved to obtain the final biologically active clostridial neurotoxin. Thus, clostridial neurotoxins may be expressed in high yield in rapidly-growing bacteria as relatively non-toxic single-chain polypeptides.

Furthermore, it might be advantageous to modify clostridial neurotoxin characteristics regarding biological activity, cell specificity, antigenic potential and duration of effect by genetic engineering to obtain recombinant neurotoxins with new therapeutic properties in specific clinical areas. Genetic modification of clostridial neurotoxins might allow altering the mode of action or expanding the range of therapeutic targets.

WO 96/39166 discloses analogues of botulinum toxin comprising amino acid residues which are more resistant to degradation in neuromuscular tissue.

Patent family based on WO 02/08268 (including family member U.S. Pat. No. 6,903,187) discloses a clostridial neurotoxin comprising a structural modification selected from addition or deletion of a leucine-based motif, which alters the biological persistence of the neurotoxin (see also: Fernández-Salas et al., Proc. Natl. Acad. Sci. U.S.A. 101 (2004) 3208-3213; Wang et al., J. Biol. Chem. 286 (2011) 6375-6385). Fernández-Salas et al. initially hypothesized that the increased persistence was due to the membrane-binding properties of the dileucine motif (see Fernández-Salas et al., loc. cit., p. 3211 and 3213). Wang et al. mention this membrane theory (see Wang et al., loc. cit., p. 6376, left column, last full paragraph, and p. 6383, first full paragraph of "Discussion"), but favor an alternative theory: the protection from degradation by proteolysis (see Wang et al., loc. cit., p. 6384, left column, lines 27ff).

US 2002/0127247 describes clostridial neurotoxins comprising modifications in secondary modification sites and exhibiting altered biological persistence.

Botulinum toxin variants exhibiting longer biological half lives in neuromuscular tissue than naturally occurring botulinum toxins would be advantageous in order to reduce administration frequency and the incidence of neutralizing antibody generation since immunologic tolerance to botulinum toxin is correlated with cumulative doses.

Furthermore, BoNT serotypes naturally exhibiting a short duration of action could potentially be effectively used in clinical applications, if their biological persistence could be enhanced. Modified BoNT/E with an increased duration of action could potentially be used in patients exhibiting an immune reaction against BoNT/A. Moreover, BoNT/E was shown to induce a more severe block of pain mediator release from sensory neurons than BoNT/A. In clinical applications where BoNT/A provides only partial pain relief or in just a subset of patients, such as in the treatment of headaches, or where BoNT/E has been found to be more effective than BoNT/A but gives only short-term therapy, such as in the treatment of epilepsy, BoNT/E with an increased duration of effect might prove useful.

There is a strong demand to produce clostridial neurotoxins with an increased duration of effect, in order to allow for reduction of administration frequency and exploitation of the therapeutic potential of BoNT serotypes, which have so far been considered impractical for clinical application due to the short half-life of the respective clinically relevant effect. Ideally, the duration of effect of a particular clostridial neurotoxin could be adjusted in a tailor-made fashion in order to address any particular features and demands of a given indication, such as the amount of neurotoxin being administered, frequency of administration etc. To date, such aspects have not been solved satisfactorily.

OBJECTS OF THE INVENTION

It was an object of the invention to provide recombinant clostridial neurotoxins exhibiting an increased duration of effect and to establish a reliable and accurate method for manufacturing and obtaining such recombinant clostridial neurotoxins. Such a method and novel precursor clostridial neurotoxins used in such methods would serve to satisfy the great need for recombinant clostridial neurotoxins exhibiting an increased duration of effect.

SUMMARY OF THE INVENTION

The naturally occurring botulinum toxin serotypes display highly divergent durations of effect, probably due to their distinct subcellular localization. BoNT/A exhibiting the longest persistence was shown to localize in the vicinity of the plasma membrane of neuronal cells, whereas the short-duration BoNT/E serotype is cytosolic. However, additional factors such as degradation, diffusion, and/or translocation rates might have a decisive impact on the differences in the duration of effect for the individual botulinum toxin serotypes.

So far, no generally applicable method for modifying clostridial neurotoxins in order to increase their duration of effect is available. Surprisingly, it has been found that recombinant clostridial neurotoxins having such effects can be obtained by cloning a sequence encoding a random coil domain into a gene encoding a parental clostridial neurotoxin, and by subsequent heterologous expression of the generated construct in recombinant host cells.

Thus, in one aspect, the present invention relates to recombinant clostridial neurotoxin comprising a random coil domain.

In another aspect, the present invention relates to a pharmaceutical composition comprising the recombinant clostridial neurotoxin of the present invention.

In yet another aspect, the present invention relates to the use of the composition of the present invention for cosmetic treatment.

In another aspect, the present invention relates to a method for the generation of the recombinant clostridial neurotoxin of the present invention, comprising the step of obtaining a recombinant nucleic acid sequence encoding a recombinant single-chain precursor clostridial neurotoxin by the insertion of a nucleic acid sequence encoding said random coil domain into a nucleic acid sequence encoding a parental clostridial neurotoxin.

In another aspect, the present invention relates to a recombinant single-chain precursor clostridial neurotoxin comprising a random coil domain.

In another aspect, the present invention relates to a nucleic acid sequence encoding the recombinant single-chain precursor clostridial neurotoxin of the present invention.

In another aspect, the present invention relates to a method for obtaining the nucleic acid sequence of the present invention, comprising the step of inserting a nucleic acid sequence encoding a random coil domain into a nucleic acid sequence encoding a parental clostridial neurotoxin.

In another aspect, the present invention relates to a vector comprising the nucleic acid sequence of the present invention, or the nucleic acid sequence obtainable by the method of the present invention.

In another aspect, the present invention relates to a recombinant host cell comprising the nucleic acid sequence of the present invention, the nucleic acid sequence obtainable by the method of the present invention, or the vector of the present invention.

In another aspect, the present invention relates to a method for producing the recombinant single-chain precursor clostridial neurotoxin of the present invention, comprising the step of expressing the nucleic acid sequence of the present invention, or the nucleic acid sequence obtainable by the method of the present invention, or the vector of the present invention in a recombinant host cell, or cultivating the recombinant host cell of the present invention under conditions that result in the expression of said nucleic acid sequence.

FIGURES

FIG. 1: Schematic Presentation of PASylated Botulinum Toxin A (PAS·rBoNT/A).

Figure 2:
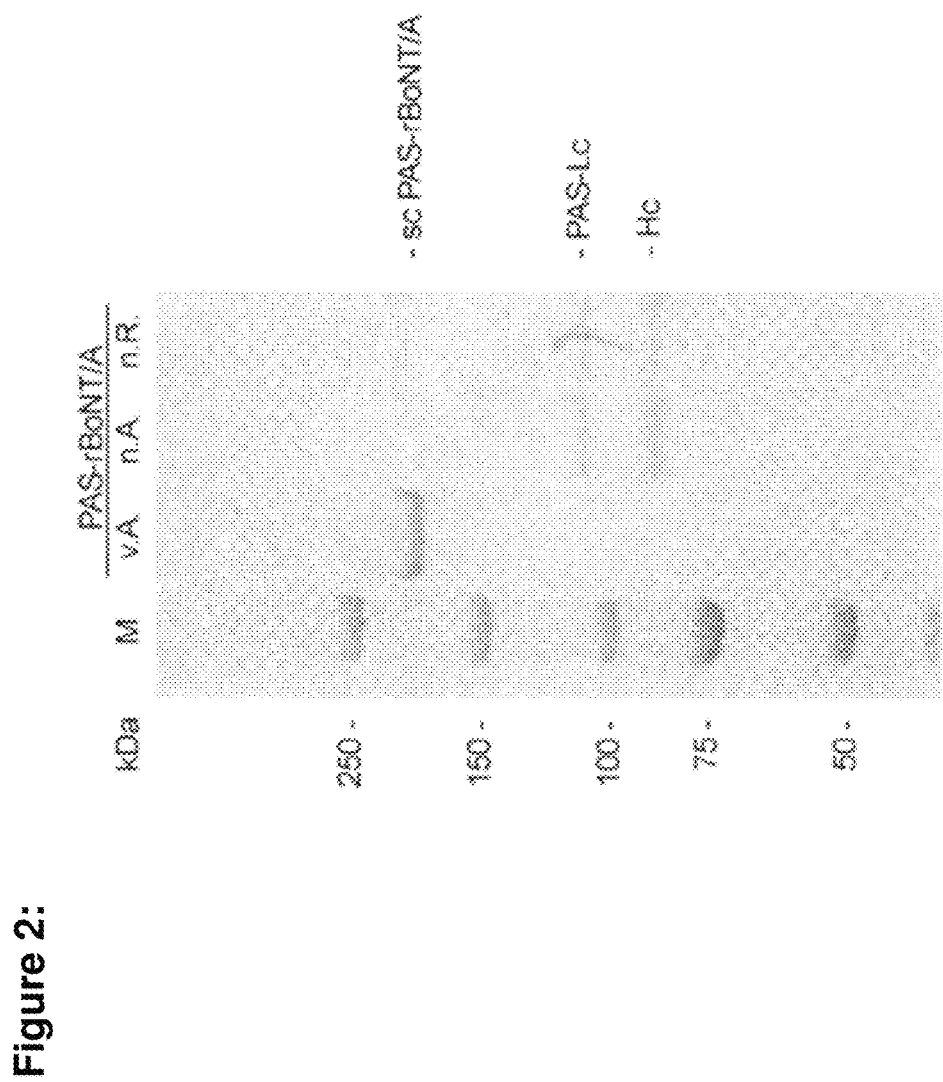

FIG. 2: SDS·PAGE of purified PAS-rBoNT/A. Prior to applying the samples to the gel, β-mercaptoethanol was added. Lane "v.A.": purified, non-activated single-chain PAS-rBoNT/A having a molecular weight (Mw) of about 175 kDa. Lanes "n.A." (after activation) and "n.R." (after purification) show light chain (PAS-Lc) and heavy chain (Hc) obtained after activation by thrombin under reducing conditions. The light chain runs with an apparent Mw of about 110 kDa well above the theoretical Mw of about 75 kDa.

Figure 3:
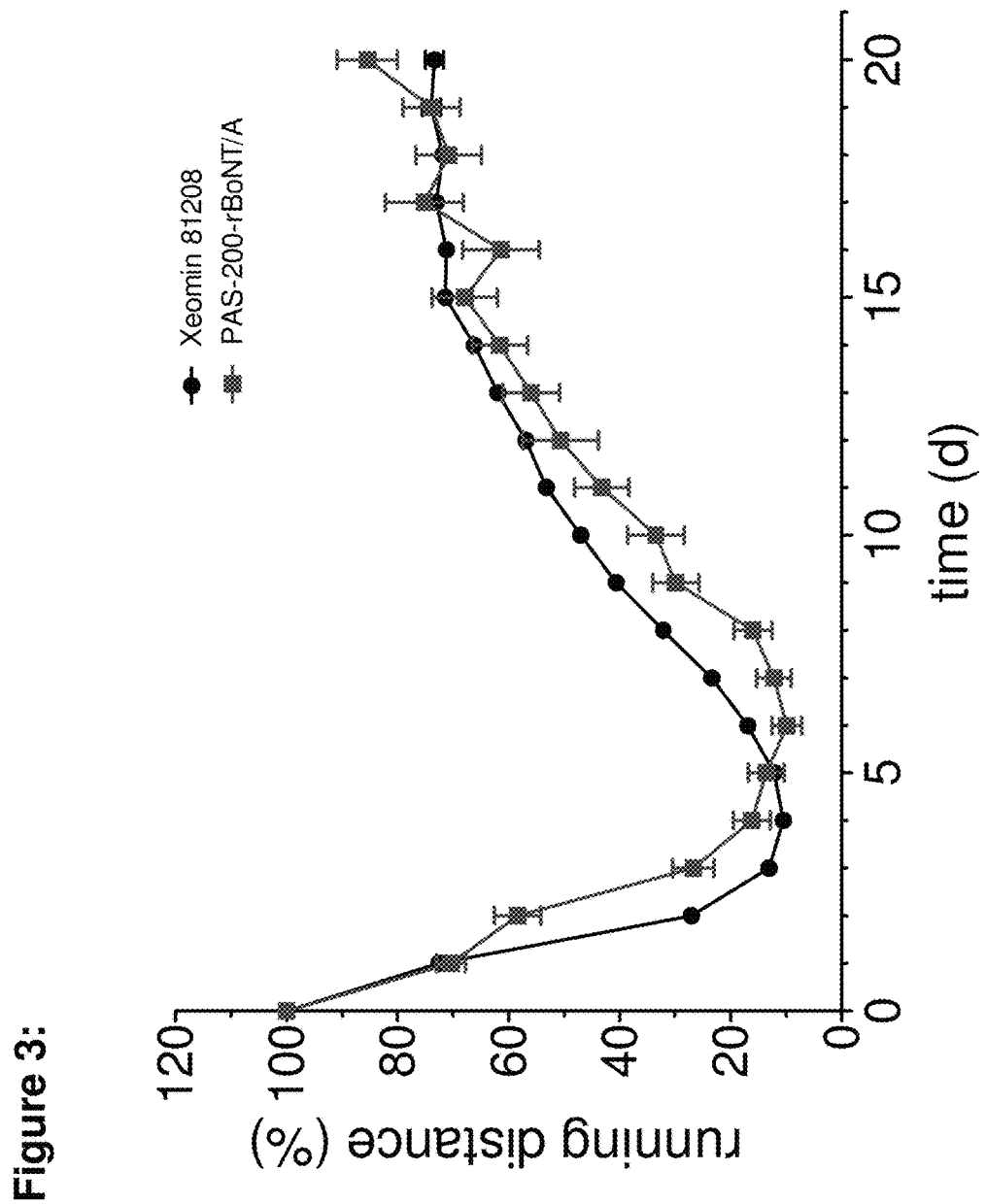

FIG. 3: Mouse running assay with PAS200-rBoNT/A: ■: PAS200-rBoNT/A; ※: mean of Standard (54 assays) from Xeomin® 81208 (0.6 U).

FIG. 4: Mouse running assay with PAS100-rBoNT/A: ■: PAS100-rBoNT/A; ※: mean of Standard (54 assays) from Xeomin® 81208 (0.6 U).

DETAILED DESCRIPTION OF THE INVENTION

The present invention may be understood more readily by reference to the following detailed description of the invention and the examples included therein.

In one aspect, the present invention relates to a recombinant clostridial neurotoxin comprising a random coil domain.

In the context of the present invention, the term "clostridial neurotoxin" refers to a natural neurotoxin obtainable from bacteria of the class Clostridia, including *Clostridium tetani* and *Clostridium botulinum*, or to a neurotoxin obtainable from alternative sources, including from recombinant technologies or from genetic or chemical modification. Particularly, the clostridial neurotoxins have endopeptidase activity.

Clostridial neurotoxins are produced as single-chain precursors that are proteolytically cleaved by an unknown clostridial endoprotease within the loop region to obtain the biologically active disulfide-linked di-chain form of the neurotoxin, which comprises two chain elements, a functionally active light chain and a functionally active heavy chain, where one end of the light chain is linked to one end of the heavy chain not via a peptide bond, but via a disulfide bond.

In the context of the present invention, the term "clostridial neurotoxin light chain" refers to that part of a clostridial neurotoxin that comprises an endopeptidase activity responsible for cleaving one or more proteins that is/are part of the so-called SNARE-complex involved in the process resulting in the release of neurotransmitter into the synaptic cleft: In naturally occurring clostridial neurotoxins, the light chain has a molecular weight of approx. 50 kDa.

In the context of the present invention, the term "clostridial neurotoxin heavy chain" refers to that part of a clostridial neurotoxin that is responsible for entry of the neurotoxin into the neuronal cell: In naturally occurring clostridial neurotoxins, the heavy chain has a molecular weight of approx. 100 kDa.

In the context of the present invention, the term "functionally active clostridial neurotoxin chain" refers to a recombinant clostridial neurotoxin chain able to perform the biological functions of a naturally occurring *Clostridium botulinum* neurotoxin chain to at least about 50%, particularly to at least about 60%, to at least about 70%, to at least about 80%, and most particularly to at least about 90%, where the biological functions of clostridial neurotoxin chains include, but are not limited to, binding of the heavy chain to the neuronal cell, entry of the neurotoxin into a neuronal cell, release of the light chain from the di-chain neurotoxin, and endopeptidase activity of the light chain. Methods for determining a neurotoxic activity can be found, for example, in WO 95/32738, which describes the reconstitution of separately obtained light and heavy chains of tetanus toxin and botulinum toxin.

In the context of the present invention, the term "about" or "approximately" means within 20%, alternatively within 10%, including within 5% of a given value or range. Alternatively, especially in biological systems, the term "about" means within about a log (i.e. an order of magnitude), including within a factor of two of a given value.

In the context of the present invention, the term "recombinant clostridial neurotoxin" refers to a composition comprising a clostridial neurotoxin that is obtained by expression of the neurotoxin in a heterologous cell such as *E. coli*, and including, but not limited to, the raw material obtained from a fermentation process (supernatant, composition after cell lysis), a fraction comprising a clostridial neurotoxin obtained from separating the ingredients of such a raw material in a purification process, an isolated and essentially pure protein, and a formulation for pharmaceutical and/or aesthetic use comprising a clostridial neurotoxin and additionally pharmaceutically acceptable solvents and/or excipients.

In the context of the present invention, the term "recombinant clostridial neurotoxin" further refers to a clostridial neurotoxin based on a parental clostridial neurotoxin additionally comprising a heterologous random coil domain, i.e. a random coil domain that is not naturally occurring in said parental clostridial neurotoxin, in particular a synthetic random coil domain, or a random coil domain from a species other than *Clostridium botulinum*, in particular a random coil domain from a human protein.

In the context of the present invention, the term "comprises" or "comprising" means "including, but not limited to". The term is intended to be open-ended, to specify the presence of any stated features, elements, integers, steps or components, but not to preclude the presence or addition of one or more other features, elements, integers, steps, components, or groups thereof. The term "comprising" thus includes the more restrictive terms "consisting of" and "consisting essentially of".

In the context of the present invention, the term "random coil domain" refers to a protein segment, which is essentially lacking a secondary structure. Random coil domains can be detected using a variety of methods, including spectroscopic methods such as circular dichroism or nuclear magnetic resonance (NMR) methods, including multidimensional NMR experiments, or crystallographic structure determinations.

In particular embodiments, said random coil domain comprises an amino acid sequence consisting of at least 50 amino acid residues forming random coil conformation, particularly between 50 and 3000 amino acid residues, more particularly between 60 and 500 amino acid residues, more particularly between 70 and 260 amino acid residues, more particularly between 80 and 240 amino acid residues, more particularly between 90 and 220 amino acid residues, particularly 100 amino acid residues, 150 amino acid residues, or 200 amino acid residues.

In particular embodiments, said random coil domain consists of alanine (A), serine (S) and proline (P) residues. These so-called "PAS" sequences (see, for example, Schlapschy et al., Protein Engineering, Design and Selection 26 (2013) 489-501; EP 2 369 005; WO 2011/144756) have been developed in order to extend the plasma half-life of pharmaceutically active proteins. It is argued that the genetic fusion with such conformationally disordered polypeptide sequences provides a simple way to attach a solvated random chain with large hydrodynamic volume to the fusion partner, for example a protein of biopharmaceutical interest, so that the size of the resulting fusion protein is significantly increased, and that by these means the typically rapid clearance of the biologically active component via kidney filtration is retarded by one to two orders of magnitude.

Surprisingly, it has been found that attachment of a random coil domain, such as a PAS-based domain, is also able to extend the duration of effect of a protein that is active intracellularly, particularly since plasma half-life of botulinum toxins has so far not been regarded as being of critical importance for their duration of effect. The extension of duration is furthermore particularly surprising, since it has been argued that macromolecular side chains such as PAS sequences or polyethylene glycol-based sequences prevent the cellular uptake, so that this way of intravasal protein stabilization could only be applied to proteins for therapeutic intervention with cell surface markers or receptors (A. Weber, Inhibierung von Stat5 in Tumoren durch RNA-Interferenz and spezifische Interaktion eines Peptidaptamer-Konstruktes mit der DNA-Bindedomäne, PhD thesis, Johann-Wolfgang-Goethe Universität, Frankfurt am Main (Germany) 2013, p. 220, final full sentence).

In particular embodiments, said random coil domain comprises a plurality of amino acid repeats, wherein said repeat consist of Ala, Ser, and Pro residues and wherein no more than six consecutive amino acid residues are identical.

In particular embodiments, the proline residues comprised in said random coil domain constitute more than 4% and less than 40% of the amino acids of said random coil domain.

In particular embodiments, said random coil domain comprises at least one amino acid sequence selected from the group consisting of: ASPAAPAPASPAAPAPSAPA (SEQ ID NO: 1); AAPASPAPAAPSAPAPAAPS (SEQ ID NO: 2); APSSPSPSAPSSPSPASPSS (SEQ ID NO: 3), SAPSSPSPSAPSSPSPASPS (SEQ ID NO: 4), SSPSAPSPSSPASPSPSSPA (SEQ ID NO: 5), AASPAAPSAPPAAASPAAPSAPPA (SEQ ID NO: 6) and ASAAAPAAASAAASAPSAAA (SEQ ID NO: 7) or circular permuted versions or (a) multimer(s) of these sequences as a whole or parts of these sequences, particularly (ASPAAPAPASPAAPAPSAPA)$_n$, with n being (i) an integer selected from 3 to 25 (SEQ ID NO: 12), more particularly from 4 to 8 (SEQ ID NO: 13), more particularly from 5 to 10 (SEQ ID NO: 14), in particular wherein n is 5 (SEQ ID NO: 15) or 10 (SEQ ID NO: 16); or (ii) an integer selected from 5 to 150 (SEQ ID NO: 17), more particularly from 6 to 20 (SEQ ID NO: 18), more particularly from 7 to 13 (SEQ ID NO: 19), more particularly from 8 to 12 (SEQ ID NO: 20), more particularly from 9 to 11 (SEQ ID NO: 21), in particular wherein n is 10 (SEQ ID NO: 16).

In particular embodiments, said random coil domain is inserted at (i) the N-terminus of the light chain of said recombinant clostridial neurotoxin; (ii) the C-terminus of the light chain of said recombinant clostridial neurotoxin; (iii) the N-terminus of the heavy chain of said recombinant clostridial neurotoxin; or (iv) the C-terminus of the heavy chain of said recombinant clostridial neurotoxin, particularly at the N-terminus of the light chain of said recombinant clostridial neurotoxin.

In particular embodiments, the sequence of said clostridial neurotoxin is selected from the sequence of (i) a *Clostridium botulinum* neurotoxin serotype A, B, C, D, E, F, and G, particularly *Clostridium botulinum* neurotoxin serotype A, C and E, particularly *Clostridium botulinum* neurotoxin serotype A, or (ii) from the sequence of a functional variant of a *Clostridium botulinum* neurotoxin of (i), or (iii) from the sequence of a chimeric *Clostridium botulinum* neurotoxin, wherein the clostridial neurotoxin light chain and heavy chain are from different parental clostridial neurotoxin serotypes.

In the context of the present invention, the term "*Clostridium botulinum* neurotoxin serotype A, B, C, D, E, F, and G" refers to neurotoxins found in and obtainable from *Clostridium botulinum*. Currently, seven serologically distinct types, designated serotypes A, B, C, D, E, F, and G are known, including certain subtypes (e.g. A1, A2, A3, A4 and A5).

In particular embodiments the clostridial neurotoxin is selected from a *Clostridium botulinum* neurotoxin serotype A, C and E, in particular from *Clostridium botulinum* neurotoxin serotype A, or from a functional variant of any such *Clostridium botulinum* neurotoxin.

In particular embodiments, said recombinant clostridial neurotoxin has a light chain and a heavy chain comprised in the amino acid sequence as found in SEQ ID NO: 8 or SEQ ID NO: 10.

In the context of the present invention, the term "functional variant of a clostridial neurotoxin" refers to a neurotoxin that differs in the amino acid sequence and/or the nucleic acid sequence encoding the amino acid sequence from a clostridial neurotoxin, but is still functionally active. In the context of the present invention, the term "functionally active" refers to the property of a recombinant clostridial neurotoxin to exhibit a biological activity of at least about 50%, particularly to at least about 60%, at least about 70%, at least about 80%, and most particularly at least about 90% of the biological activity of a naturally occurring parental clostridial neurotoxin, i.e. a parental clostridial neurotoxin without random coil domain, where the biological functions include, but are not limited to, binding to the neurotoxin receptor, entry of the neurotoxin into a neuronal cell, release of the light chain from the two-chain neurotoxin, and endopeptidase activity of the light chain, and thus inhibition of neurotransmitter release from the affected nerve cell.

On the protein level, a functional variant will maintain key features of the corresponding clostridial neurotoxin, such as key residues for the endopeptidase activity in the light chain, or key residues for the attachment to the neurotoxin receptors or for translocation through the endosomal membrane in the heavy chain, but may contain one or more mutations comprising a deletion of one or more amino acids of the corresponding clostridial neurotoxin, an addition of one or more amino acids of the corresponding clostridial neurotoxin, and/or a substitution of one or more amino acids of the corresponding clostridial neurotoxin. Particularly, said deleted, added and/or substituted amino acids are consecutive amino acids. According to the teaching of the present invention, any number of amino acids may be added, deleted, and/or substituted, as long as the functional variant remains biologically active. For example, 1, 2, 3, 4, 5, up to 10, up to 15, up to 25, up to 50, up to 100, up to 200, up to 400, up to 500 amino acids or even more amino acids may be added, deleted, and/or substituted. Accordingly, a functional variant of the neurotoxin may be a biologically active fragment of a naturally occurring neurotoxin. This neurotoxin fragment may contain an N-terminal, C-terminal, and/or one or more internal deletion(s).

In another embodiment, the functional variant of a clostridial neurotoxin additionally comprises a signal peptide. Usually, said signal peptide will be located at the N-terminus of the neurotoxin. Many such signal peptides are known in the art and are comprised by the present invention. In particular, the signal peptide results in transport of the neurotoxin across a biological membrane, such as the membrane of the endoplasmic reticulum, the Golgi membrane or the plasma membrane of a eukaryotic or prokaryotic cell. It has been found that signal peptides, when attached to the neurotoxin, will mediate secretion of the neurotoxin into the supernatant of the cells. In certain embodiments, the signal peptide will be cleaved off in the course of, or subsequent to, secretion, so that the secreted protein lacks the N-terminal signal peptide, is composed of separate light and heavy chains, which are covalently linked by disulfide bridges, and is proteolytically active.

In particular embodiments, the functional variant has in its *clostridium* neurotoxin part a sequence identity of at least about 40%, at least about 50%, at least about 60%, at least about 70% or most particularly at least about 80%, and a sequence homology of at least about 60%, at least about 70%, at least about 80%, at least about 90%, or most particularly at least about 95% to the corresponding part in the parental clostridial neurotoxin. Methods and algorithms for determining sequence identity and/or homology, including the comparison of variants having deletions, additions, and/or substitutions relative to a parental sequence, are well known to the practitioner of ordinary skill in the art. On the DNA level, the nucleic acid sequences encoding the functional homologue and the parental clostridial neurotoxin may differ to a larger extent due to the degeneracy of the genetic code. It is known that the usage of codons is different between prokaryotic and eukaryotic organisms. Thus, when expressing a prokaryotic protein such as a clostridial neurotoxin, in a eukaryotic expression system, it may be necessary, or at least helpful, to adapt the nucleic acid sequence to the codon usage of the expression host cell, meaning that sequence identity or homology may be rather low on the nucleic acid level.

In the context of the present invention, the term "variant" refers to a neurotoxin that is a chemically, enzymatically, or genetically modified derivative of a corresponding clostridial neurotoxin, including chemically or genetically modified neurotoxin from *C. botulinum*, particularly of *C. botulinum* neurotoxin serotype A, C or E. A chemically modified derivative may be one that is modified by pyruvation, phosphorylation, sulfatation, lipidation, pegylation, glycosylation and/or the chemical addition of an amino acid or a polypeptide comprising between 2 and about 100 amino acids, including modification occurring in the eukaryotic host cell used for expressing the derivative. An enzymatically modified derivative is one that is modified by the activity of enzymes, such as endo- or exoproteolytic enzymes, including modification by enzymes of the eukaryotic host cell used for expressing the derivative. As pointed out above, a genetically modified derivative is one that has been modified by deletion or substitution of one or more amino acids contained in, or by addition of one or more amino acids (including polypeptides comprising between 2 and about 100 amino acids) to, the amino acid sequence of said clostridial neurotoxin. Methods for designing and constructing such chemically or genetically modified derivatives and for testing of such variants for functionality are well known to anyone of ordinary skill in the art.

In particular embodiments, said recombinant clostridial neurotoxin shows increased duration of effect relative to an identical clostridial neurotoxin without the random coil domain.

In the context of the present invention, the term "increased duration of effect" or "increased duration of action" refers to a longer lasting denervation mediated by a clostridial neurotoxin of the present invention. For example, as disclosed herein, administration of a disulfide-linked di-chain clostridial neurotoxin comprising a random coil domain results in localized paralysis for a longer period of time relative to administration of an identical disulfide-linked di-chain clostridial neurotoxin without the coiled coil domain.

In the context of the present invention, the term "increased duration of effect/action" is defined as a more than about 20%, particularly more than about 50%, more particularly more than about 90% increased duration of effect of the recombinant neurotoxin of the present invention relative to the identical neurotoxin without the random coil domain.

In the context of the present invention the term "denervation" refers to denervation resulting from administration of a chemodenervating agent, for example a neurotoxin.

In the context of the present invention, the term "localized denervation" or "localized paralysis" refers to denervation of a particular anatomical region, usually a muscle or a group of anatomically and/or physiologically related muscles, which results from administration of a chemodenervating agent, for example a neurotoxin, to the particular anatomical region.

Without wishing to be bound by theory, the recombinant clostridial neurotoxins of the present invention might show increased biological half-life, reduced degradation rates, decreased diffusion rates, increased uptake by neuronal cells, and/or modified intracellular translocation rates, in each case relative to an identical parental clostridial neurotoxin without the random coil domain.

In particular embodiments, the increased duration of effect is due to an increased biological half-life.

In the context of the present invention, the term "biological half-life" specifies the lifespan of a protein, for example of a clostridial neurotoxin, in vivo. In the context of the present invention, the term "biological half-life" refers to the period of time, by which half of a protein pool is degraded in vivo. For example it refers to the period of time, by which half of the amount of clostridial neurotoxin of one administered dosage is degraded.

In the context of the present invention, the term "increased biological half-life" is defined as a more than about 20%, particularly more than about 50%, more particularly more than about 90% increased biological half-life of the recombinant neurotoxin of the present invention relative to the identical neurotoxin without the random coil domain.

In the context of the present invention, the term "reduced degradation rate" means that the random coil domain (PAS sequence) protects the light chain against degradation processes in the cytosol of the neuron such as, for example, the attack of proteases or modifying enzymes like E3 ligases. Because of this protection the half-life of the light chain in the neuron is extended resulting in a longer duration of the therapeutic effect.

In particular embodiments, the recombinant clostridial neurotoxin is for the use in the treatment of a disease requiring improved chemodenervation, wherein the recombinant clostridial neurotoxin causes longer lasting denervation relative to an identical clostridial neurotoxin without the random coil domain.

In particular other embodiments, the recombinant clostridial neurotoxin is for use in the treatment of (a) patients showing an immune reaction against BoNT/A, or (b) headache or epilepsy, wherein the recombinant clostridial neurotoxin is of serotype E.

In another aspect, the present invention relates to a pharmaceutical composition comprising the recombinant clostridial neurotoxin of the present invention.

In particular embodiments, the recombinant clostridial neurotoxin of the present invention or the pharmaceutical composition of the present invention is for use in the treatment of a disease or condition taken from the list of: cervical dystonia (spasmodic torticollis), blepharospasm, severe primary axillary hyperhidrosis, achalasia, lower back pain, benign prostate hypertrophy, chronic focal painful neuropathies, migraine and other headache disorders.

Additional indications where treatment with botulinum neurotoxins is currently under investigation and where the pharmaceutical composition of the present invention may be used, include pediatric incontinence, incontinence due to overactive bladder, and incontinence due to neurogenic bladder, anal fissure, spastic disorders associated with injury or disease of the central nervous system including trauma, stroke, multiple sclerosis, Parkinson's disease, or cerebral palsy, focal dystonias affecting the limbs, face, jaw or vocal cords, temporomandibular joint (TMJ) pain disorders, diabetic neuropathy, wound healing, excessive salivation, vocal cord dysfunction, reduction of the Masseter muscle for decreasing the size of the lower jaw, treatment and prevention of chronic headache and chronic musculoskeletal pain, treatment of snoring noise, assistance in weight loss by increasing the gastric emptying time.

Most recently, clostridial neurotoxins have been evaluated for the treatment of other new indications, for example painful keloid, diabetic neuropathic pain, refractory knee pain, trigeminal neuralgia trigger-zone application to control pain, scarring after cleft-lip surgery, cancer and depression.

In yet another aspect, the present invention relates to the use of the composition of the present invention for cosmetic treatment.

In the context of the present invention, the term "cosmetic treatment" relates to uses in cosmetic or aesthetic applications, such as the treatment of wrinkles, crow's feet, frown lines etc.

In another aspect, the present invention relates to a method for the generation of the recombinant clostridial neurotoxin of the present invention, comprising the step of obtaining a recombinant nucleic acid sequence encoding a recombinant single-chain precursor clostridial neurotoxin by the insertion of a nucleic acid sequence encoding said random coil domain into a nucleic acid sequence encoding a parental clostridial neurotoxin.

In the context of the present invention, the term "recombinant nucleic acid sequence" refers to a nucleic acid, which has been generated by joining genetic material from two different sources.

In the context of the present invention, the term "single-chain precursor clostridial neurotoxin" refers to a single-chain precursor for a disulfide-linked di-chain clostridial neurotoxin, comprising a functionally active clostridial neurotoxin light chain, a functionally active neurotoxin heavy chain, and a loop region linking the C-terminus of the light chain with the N-terminus of the heavy chain.

In the context of the present invention, the term "recombinant single-chain precursor clostridial neurotoxin" refers to a single-chain precursor clostridial neurotoxin comprising a heterologous random coil domain, i.e. a random coil domain from a species other than *Clostridium botulinum*.

In particular embodiments, the recombinant single-chain precursor clostridial neurotoxin comprises a protease cleavage site in said loop region.

Single-chain precursor clostridial neurotoxins have to be proteolytically cleaved to obtain the final biologically active clostridial neurotoxins. Proteolytic cleavage may either occur during heterologous expression by host cell enzymes, or by adding proteolytic enzymes to the raw protein material isolated after heterologous expression. Naturally occurring clostridial neurotoxins usually contain one or more cleavage signals for proteases which post-translationally cleave the single-chain precursor molecule, so that the final di- or multimeric complex can form. At present, clostridial neurotoxins are still predominantly produced by fermentation processes using appropriate *Clostridium* strains. During the fermentation process, the single-chain precursors are proteolytically cleaved by an unknown clostridial protease to obtain the biologically active di-chain clostridial neurotoxin. In cases, where the single-chain precursor molecule is the precursor of a protease, autocatalytic cleavage may occur. Alternatively, the protease can be a separate non-clostridial enzyme expressed in the same cell. WO 2006/076902 describes the proteolytic cleavage of a recombinant clostridial neurotoxin single-chain precursor at a heterologous recognition and cleavage site by incubation of the *E. coli* host cell lysate. The proteolytic cleavage is carried out by an unknown *E. coli* protease. In certain applications of recombinant expression, modified protease cleavage sites have been introduced recombinantly into the interchain region between the light and heavy chain of clostridial toxins, e.g. protease cleavage sites for human thrombin or non-human proteases (see WO 01/14570).

In particular embodiments, the protease cleavage site is a site that is cleaved by a protease selected from the list of: a protease selected from the list of: thrombin, trypsin, enterokinase, factor Xa, plant papain, insect papain, crustacean papain, enterokinase, human rhinovirus 3C protease, human enterovirus 3C protease, tobacco etch virus protease, Tobacco Vein Mottling Virus, subtilisin and caspase 3.

In a particular embodiment, the recombinant single-chain precursor clostridial neurotoxin further comprises a binding tag, particularly selected from the group comprising: glutathione-S-transferase (GST), maltose binding protein (MBP), a His-tag, a Strep-tag®, or a FLAG-tag.

In the context of the present invention, the term "parental clostridial neurotoxin" refers to an initial clostridial neurotoxin without a heterologous random coil domain, selected from a natural clostridial neurotoxin, a functional variant of a natural clostridial neurotoxin or a chimeric clostridial neurotoxin, wherein the clostridial neurotoxin light chain and heavy chain are from different clostridial neurotoxin serotypes.

In particular embodiments, the method for the generation of the recombinant clostridial neurotoxin of the present invention further comprises the step of heterologously expressing said recombinant nucleic acid sequence in a host cell, particularly in a bacterial host cell, more particularly in an *E. coli* host cell.

In certain embodiments, the *E. coli* cells are selected from *E. coli* XL1-Blue, Nova Blue, TOP10, XL10-Gold, BL21, and K12.

In particular embodiments, the method for the generation of the recombinant clostridial neurotoxin of the present invention additionally comprises at least one of the steps of (i) generating a disulfide-linked di-chain recombinant clostridial neurotoxin comprising a random coil domain by causing or allowing contacting of said recombinant single-chain precursor clostridial neurotoxin with an endoprotease and (ii) purification of said recombinant single-chain precursor clostridial neurotoxin or said disulfide-linked di-chain recombinant clostridial neurotoxin by chromatography.

In particular embodiments, the recombinant single-chain precursor clostridial neurotoxin, or the recombinant disulfide-linked di-chain clostridial neurotoxin, is purified after expression, or in the case of the recombinant disulfide-linked di-chain clostridial neurotoxin, after the cleavage reaction. In particular such embodiments, the protein is purified by chromatography, particularly by immunoaffinity chromatography, or by chromatography on an ion exchange matrix, a hydrophobic interaction matrix, or a multimodal chromatography matrix, particularly a strong ion exchange matrix, more particularly a strong cation exchange matrix.

In the context of the present invention, the term "causing . . . contacting of said recombinant single-chain precursor clostridial neurotoxin . . . with an endoprotease" refers to an active and/or direct step of bringing said neurotoxin and said endoprotease in contact, whereas the term "allowing contacting of a recombinant single-chain precursor clostridial neurotoxin . . . with an endoprotease" refers to an indirect step of establishing conditions in such a way that said neurotoxin and said endoprotease are getting in contact to each other.

In the context of the present invention, the term "endoprotease" refers to a protease that breaks peptide bonds of non-terminal amino acids (i.e. within the polypeptide chain). As they do not attack terminal amino acids, endoproteases cannot break down peptides into monomers.

In particular embodiments, cleavage of the recombinant single-chain precursor clostridial neurotoxin is near-complete.

In the context of the present invention, the term "near-complete" is defined as more than about 95% cleavage, particularly more than about 97.5%, more particularly more than about 99% as determined by SDS-PAGE and subsequent Western Blot or reversed phase chromatography.

In particular embodiments, cleavage of the recombinant single-chain precursor clostridial neurotoxin occurs at a heterologous cleavage signal located in the loop region of the recombinant precursor clostridial neurotoxin.

In particular embodiments, the cleavage reaction is performed with crude host cell lysates containing said single-chain precursor protein.

In other particular embodiments, the single-chain precursor protein is purified or partially purified, particularly by a first chromatographic enrichment step, prior to the cleavage reaction.

In the context of the present invention, the term "purified" relates to more than about 90% purity. In the context of the present invention, the term "partially purified" relates to purity of less than about 90% and an enrichment of more than about two fold.

In another aspect, the present invention relates to a recombinant single-chain clostridial neurotoxin, which is a precursor for the recombinant clostridial neurotoxin of the present invention Thus, in such aspect, the present invention relates to a recombinant single-chain precursor clostridial neurotoxin comprising a random coil domain.

In particular embodiments, said random coil domain comprises an amino acid sequence consisting of at least 50 amino acid residues forming random coil conformation, particularly between 50 and 3000 amino acid residues, more particularly between 60 and 500 amino acid residues, more particularly between 70 and 260 amino acid residues, more particularly between 80 and 240 amino acid residues, more particularly between 90 and 220 amino acid residues, particularly 100 amino acid residues, 150 amino acid residues, or 200 amino acid residues.

In particular embodiments, said random coil domain consists of alanine, serine and proline residues.

In particular embodiments, said random coil domain comprises a plurality of amino acid repeats, wherein said repeat consist of Ala, Ser, and Pro residues and wherein no more than 6 consecutive amino acid residues are identical.

In particular embodiments, the proline residues comprised in said random coil domain constitute more than 4% and less than 40% of the amino acids of said random coil domain.

In particular embodiments, said random coil domain comprises at least one amino acid sequence selected from the group consisting of: ASPAAPAPASPAAPAPSAPA (SEQ ID NO: 1); AAPASPAPAAPSAPAPAAPS (SEQ ID NO: 2); APSSPSPSAPSSPSPASPSS (SEQ ID NO: 3), SAPSSPSPSAPSSPSPASPS (SEQ ID NO: 4), SSPSAPSPSSPASPSPSSPA (SEQ ID NO: 5), AASPAAPSAPPAAASPAAPSAPPA (SEQ ID NO: 6) and ASAAAPAAASAAASAPSAAA (SEQ ID NO: 7) or circular permuted versions or (a) multimer(s) of these sequences as a whole or parts of these sequences, particularly (ASPAAPAPASPAAPAPSAPA)$_n$, with n being (i) an integer selected from 3 to 25 (SEQ ID NO: 12), more particularly from 4 to 8 (SEQ ID NO: 13), more particularly from 5 to 10 (SEQ ID NO: 14), in particular wherein n is 5 (SEQ ID NO: 15) or 10 (SEQ ID NO: 16); or (ii) an integer selected from 5 to 150 (SEQ ID NO: 17), more particularly from 6 to 20 (SEQ ID NO: 18), more particularly from 7 to 13 (SEQ ID NO: 19), more particularly from 8 to 12 (SEQ ID NO: 20), more particularly from 9 to 11 (SEQ ID NO: 21), in particular wherein n is 10 (SEQ ID NO: 16).

In particular embodiments, said random coil domain is inserted at (i) the N-terminus of the light chain of said recombinant clostridial neurotoxin; (ii) the C-terminus of the light chain of said recombinant clostridial neurotoxin; (i) the N-terminus of the heavy chain of said recombinant clostridial neurotoxin; or (ii) the C-terminus of the heavy chain of said recombinant clostridial neurotoxin.

In particular embodiments, the sequence of said clostridial neurotoxin is selected from the sequence of (i) a *Clostridium botulinum* neurotoxin serotype A, B, C, D, E, F, and G, particularly *Clostridium botulinum* neurotoxin serotype A, C and E, more particularly *Clostridium botulinum* neurotoxin serotype A, or (ii) from the sequence of a functional variant of a *Clostridium botulinum* neurotoxin of (i), or (iii) from the sequence of a chimeric *Clostridium botulinum* neurotoxin, wherein the clostridial neurotoxin light chain and heavy chain are from different clostridial neurotoxin serotypes.

In particular embodiments, said recombinant single-chain clostridial neurotoxin has the amino acid sequence as found in SEQ ID NO: 8 or SEQ ID NO: 10 (see Table 1).

In another aspect, the present invention relates to a nucleic acid sequence encoding the recombinant single-chain clostridial neurotoxin of the present invention, particularly a nucleic acid sequence as found in SEQ ID NO: 9 or SEQ ID NO: 11 (see Table 1).

In another aspect, the present invention relates to a method for obtaining the nucleic acid sequence of the present invention, comprising the step of inserting a nucleic acid sequence encoding a random coil domain into a nucleic acid sequence encoding a parental clostridial neurotoxin.

In another aspect, the present invention relates to a vector comprising the nucleic acid sequence of the present invention, or the nucleic acid sequence obtainable by the method of the present invention.

In another aspect, the present invention relates to a recombinant host cell comprising the nucleic acid sequence of the present invention, the nucleic acid sequence obtainable by the method of the present invention, or the vector of the present invention.

In certain embodiments, the recombinant host cells are selected from *E. coli* XL1-Blue, Nova Blue, TOP10, XL10-Gold, BL21, and K12.

In another aspect, the present invention relates to a method for producing the recombinant single-chain precursor clostridial neurotoxin of the present invention, comprising the step of expressing the nucleic acid sequence of the present invention, or the nucleic acid sequence obtainable by the method of the present invention, or the vector of the present invention in a recombinant host cell, or cultivating the recombinant host cell of the present invention under conditions that result in the expression of said nucleic acid sequence.

EXAMPLES

Example 1

Generation and Purification of a PASylated Botulinum Toxin Type A (PAS200-rBoNT/A)

The "PAS" module comprising 200 amino acid residues built from the amino acids proline, serine and alanine was synthetically produced and after digestion with SapI inserted at the N-terminus of recombinant BoNT/A (rBoNT/A) (FIG. 1). The correct cloning was verified by sequencing.

Expression was performed in expression strain *E. coli* BI21. Purification was done using a combination of affinity and size exclusion chromatography, followed by activation using thrombin. FIG. 2 summarizes the results of purification and activation.

Example 2

Measurement of Biological Activity in the Hemidiaphragma Test (HDA Test)

This ex vivo test performs all steps required for intoxication (target cell binding, internalization and translocation into cytosol). In order to achieve that, a murine nerve-muscle preparation, comprising the hemidiaphragma and the Nervus phrenicus, is stimulated in an organ bath by a continuous frequency of 1 Hz. The resulting amplitude of muscle contraction is plotted against the time. After addition of the toxin sample to the organ bath, the time required for a 50% reduction of the amplitude seen without toxin is determined. This so-called paralytic half-time is a direct measure for the biological activity. In the case of PAS200-rBoNT/A, the paralytic half-time was 157 min at a concentration of 0.35 ng/ml in the organ bath. By comparison with a calibration curve established with wild-type BoNT/A, a specific biological activity of 60 pg/U can be calculated.

Example 4

Duration of Effect of PAS200-rBoNT/A in a "Mouse Running Assay"

Based on the results for the activity obtained in the DAS test (see Example 3) dosages can be calculated that are suitable for a comparison of the duration of effect with a standard (Xeomin®) run in parallel. The aim is to apply an equipotent dose i.e. the maximum effect of sample and standard (Xeomin®) should be the same. Equipotent dosages of PAS200-rBoNT/A or Xeomin® were injected into the M. gastrocnemius of eight mice each that had been trained in a treadmill. Using these dosages, only a submaximum paralysis was observed in order to exclude potential systemic effects as far as possible, which may have an impact on the duration of effect. The daily running distance in the treadmill was measured over 15 days. The paralysis caused by the toxins was plotted as percentage of the running distance on the day before the injection, which was set as 100%, against the time (see FIG. 3).

The injection of PAS200-rBoNT/A resulted in a maximum paralysis after 4 days corresponding to that seen for the control group treated with Xeomin®. During the recovery phase following the phase of maximum paralysis the running distance of the control group reached a value of 25% of the starting value after 8 days, whereas the group treated with PAS200-rBoNT/A reached that value only after 11 days. Thus, the duration of effective paralysis was significantly extended.

Example 5

Generation and Purification of a PASylated Botulinum Toxin Type A (PAS100-rBoNT/A)

PAS100-rBoNT/A comprising a "PAS" module comprising 100 amino acid residues built from the amino acids proline, serine and alanine was generated and purified as described for PAS200-rBoNT/A in Example 1.

Example 6

Duration of Effect of PAS100-rBoNT/A in a "Mouse Running Assay"

A mouse running assay using PAS100-rBoNT/A was performed as described in example 4. Equipotent dosages of PAS100-rBoNT/A or Xeomin® were injected into the M. gastrocnemius of eight mice each and the daily running distance in the treadmill was measured over 15 days. The paralysis caused by the toxins was plotted as percentage of the running distance on the day before the injection, which was set as 100%, against the time (see FIG. 4).

The injection of PAS100-rBoNT/A resulted in a maximum paralysis after 6 days, for the control group treated with Xeomin® maximum paralysis was observed after 4 days. During the recovery phase the running distance of the control group reached a value of 40% of the starting value 4 days after maximum paralysis was observed (day 8), whereas the group treated with PAS100-rBoNT/A reached that value 5 days after maximum paralysis (day 11). Thus, the duration of effective paralysis was significantly extended.

TABLE 1

Sequences

SEQ ID NO 1:
ASPAAPAPASPAAPAPSAPA

SEQ ID NO 2:
AAPASPAPAAPSAPAPAAPS

SEQ ID NO 3:
APSSPSPSAPSSPSPSASPSS

SEQ ID NO 4:
SAPSSPSPSAPSSPSPASPS

TABLE 1-continued

Sequences

SEQ ID NO 5:
SSPSAPSPSSPASPSPSSPA

SEQ ID NO 6:
AASPAAPSAPPAAASPAAPSAPPA

SEQ ID NO 7:
ASAAAPAAASAAASAPSAAA

SEQ ID NO 8: PAS200 rBoNT/A (amino acid sequence)
MGSSHHHHHHGSLVPRSSSASPAAPAPASP
AAPAPSAPAASPAAPAPASPAAPAPSAPAA
SPAAPAPASPAAPAPSAPAASPAAPAPASP
AAPAPSAPAASPAAPAPASPAAPAPSAPAA
SPAAPAPASPAAPAPSAPAASPAAPAPASP
AAPAPSAPAASPAAPAPASPAAPAPSAPAA
SPAAPAPASPAAPAPSAPAASPAAPAPASP
AAPAPSAPAAPFVNKQFNYKDPVNGVDIAY
IKIPNAGQMQPVKAFKIHNKIWVIPERDTF
TNPEEGDLNPPPEAKQVPVSYYDSTYLSTD
NEKDNYLKGVTKLFERIYSTDLGRMLLTSI
VRGIPFWGGSTIDTELKVIDTNCINVIQPD
GSYRSEELNLVIIGPSADIIQFECKSFGHE
VLNLTRNGYGSTQYIRFSPDFTFGFEESLE
VDTNPLLGAGKFATDPAVTLAHELIHAGHR
LYGIAINPNRVFKVNTNAYYEMSGLEVSFE
ELRTFGGHDAKFIDSLQENEFRLYYYNKFK
DIASTLNKAKSIVGTTASLQYMKNVFKEKY
LLSEDTSGKFSVDKLKFDKLYKMLTEIYTE
DNFVKFFKVLNRKTYLNFDKAVFKINIVPK
VNYTIYDGFNLRNTNLAANFNGQNTEINNM
NFTKLKNFTGLFEFYKLLCVRGIITSKAGA
GKSLVPRGSAGAGALNDLCIKVNNWDLFFS
PSEDNFTNDLNKGEEITSDTNIEAAEENIS
LDLIQQYYLTFNFDNEPENISIENLSSDII
GQLELMPNIERFPNGKKYELDKYTMFHYLR
AQEFEHGKSRIALTNSVNEALLNPSRVYTF
FSSDYVKKVNKATEAAMFLGWVEQLVYDFT
DETSEVSTTDKIADITIIIPYIGPALNIGN
MLYKDDFVGALIFSGAVILLEFIPEIAIPV
LGTFALVSYIANKVLTVQTIDNALSKRNEK
WDEVYKYIVTNWLAKVNTQIDLIRKKMKEA
LENQAEATKAIINYQYNQYTEEEKNNINFN
IDDLSSKLNESINKAMININKFLNQCSVSY
LMNSMIPYGVKRLEDFDASLKDALLKYIYD
NRGTLIGQVDRLKDKVNNTLSTDIPFQLSK
YVDNQRLLSTFTEYIKNIINTSILNLRYES
NHLIDLSRYASKINIGSKVNFDPIDKNQIQ
LFNLESSKIEVILKNAIVYNSMYENFSTSF
WIRIPKYFNSISLNNEYTIINCMENNSGWK
VSLNYGEIIWTLQDTQEIKQRVVFKYSQMI
NISDYINRWIFVTITNNRLNNSKIYINGRL
IDQKPISNLGNIHASNNIMFKLDGCRDTHR
YIWIKYFNLFDKELNEKEIKDLYDNQSNSG
ILKDFWGDYLQYDKPYYMLNLYDPNKYVDV
NNVGIRGYMYLKGPRGSVMTTNIYLNSSLY
RGTKFIIKKYASGNKDNIVRNNDRVYINVV
VKNKEYRLATNASQAGVEKILSALEIPDVG
NLSQVVVMKSKNDQGITNKCKMNLQDNNGN
DIGFIGFHQFNNIAKLVASNWYNRQIERSS
RTLGCSWEFIPVDDGWGERPLGDLVPRGSA
NSSSVDKLWSHPQFEK SEQ ID NO 9: PAS100 rBoNT/A (amino acid sequence)
MGSSHHHHHHGSLVPRSSSASPAAPAPASP
AAPAPSAPAASPAAPAPASPAAPAPSAPAA
SPAAPAPASPAAPAPSAPAASPAAPAPASP
AAPAPSAPAASPAAPAPASPAAPAPSAPAA
PFVNKQFNYKDPVNGVDIAYIKIPNAGQMQ
PVKAFKIHNKIWVIPERDTFTNPEEGDLNP
PPEAKQVPVSYYDSTYLSTDNEKDNYLKGV
TKLFERIYSTDLGRMLLTSIVRGIPFWGGS
TIDTELKVIDTNCINVIQPDGSYRSEELNL
VIIGPSADIIQFECKSFGHEVLNLTRNGYG
STQYIRFSPDFTFGFEESLEVDTNPLLGAG
KFATDPAVTLAHELIHAGHRLYGIAINPNR
VFKVNTNAYYEMSGLEVSFEELRTFGGHDA TABLE 1-continued Sequences KFIDSLQENEFRLYYYNKFKDIASTLNKAK
SIVGTTASLQYMKNVFKEKYLLSEDTSGKF
SVDKLKFDKLYKMLTEIYTEDNFVKFFKVL
NRKTYLNFDKAVFKINIVPKVNYTIYDGFN
LRNTNLAANFNGQNTEINNMNFTKLKNFTG
LFEFYKLLCVRGIITSKAGAGKSLVPRGSA
GAGALNDLCIKVNNWDLFFSPSEDNFTNDL
NKGEEITSDTNIEAAEENISLDLIQQYYLT
FNFDNEPENISIENLSSDIIGQLELMPNIE
RFPNGKKYELDKYTMPHYLRAQEFEHGKSR
IALTNSVNEALLNPSRVYTFFSSDYVKKVN
KATEAAMFLGWVEQLVYDFTDETSEVSTTD
KIADITIIIPYIGPALNIGNMLYKDDFVGA
LIFSGAVILLEFIPEIAIPVLGTFALVSYI
ANKVLTVQTIDNALSKRNEKWDEVYKYIVT
NWLAKVNTQIDLIRKKMKEALENQAEATKA
IINYQYNQYTEEEKNNINFNIDDLSSKLNE
SINKAMININKFLNQCSVSYLMNSMIPYGV
KRLEDFDASLKDALLKYIYDNRGTLIGQVD
RLKDKVNNTLSTDIPFQLSKYVDNQRLLST
FTEYIKNIINTSILNLRYESNHLIDLSRYA
SKINIGSKVNFDPIDKNQIQLFNLESSKIE
VILKNAIVYNSMYENFSTSFWIRIPKYFNS
ISLNNEYTIINCMENNSGWKVSLNYGEIIW
TLQDTQEIKQRVVFKYSQMINISDYINRWI
FVTITNNRLNNSKIYINGRLIDQKPISNLG
NIHASNNIMFKLDGCRDTHRYIWIKYFNLF
DKELNEKEIKDLYDNQSNSGILKDFWGDYL
QYDKPYYMLNLYDPNKYVDVNNVGIRGYMY
LKGPRGSVMTTNIYLNSSLYRGTKFIIKKY
ASGNKDNIVRNNDRVYINVVVKNKEYRLAT
NASQAGVEKILSALEIPDVGNLSQVVVMKS
KNDQGITNKCKMNLQDNNGNDIGFIGFHQF
NNIAKLVASNWYNRQIERSSRTLGCSWEFI
PVDDGWGERPLGDLVPRGSANSSSVDKLWS
HPQFEK SEQ ID NO 10: PAS200 rBoNT/A (nucleic acid
sequence)
ATGGGCAGCAGCCATCATCATCACCATCAT
GGTAGCCTGGTTCCGCGTAGCTCTTCTGCA
AGTCCGGCAGCACCGGCACCGGCTTCACCA
GCTGCACCAGCACCTAGCGCACCGGCAGCA
TCTCCAGCAGCCCCTGCACCGGCAAGCCCT
GCAGCTCCAGCACCGTCAGCACCAGCAGCA
AGCCCAGCTGCTCCTGCTCCAGCGAGCCCA
GCAGCGCCAGCTCCTAGTGCCCCTGCTGCC
TCTCCTGCTGCTCCGGCACCAGCAAGTCCT
GCTGCGCCTGCACCGAGTGCTCCGGCTGCT
AGTCCTGCCGCACCAGCTCCGGCTAGTCCA
GCTGCTCCAGCCCCTTCAGCTCCGGCAGCT
TCCCCTGCAGCGCCTGCCCCTGCCAGTCCA
GCGGCTCCTGCACCTAGTGCGCCTGCAGCT
TCACCGGCTGCCCCTGCGCCAGCTTCTCCT
GCGGCTCCAGCTCCATCTGCCCCAGCCGCA
TCCCCAGCGCCACCAGCTCCAGCTTCTCCG
GCAGCGCCAGCACCTTCTGCGCCTGCCGCA
TCTCCTGCAGCACCAGCGCCTGCGAGTCCT
GCAGCTCCTGCTCCTTCAGCCCCTGCGGCA
AGTCCAGCAGCACCAGCCCCAGCAAGCCCA
GCCGCACCAGCACCATCTGCCCCTGCAGCA
CCATTTGTGAACAAGCAGTTTAACTATAAG
GACCCGGTGAACGGTGTGGATATCGCGTAT
ATCAAAATCCCGAATGCGGGCCAGATGCAA
CCAGTCAAGGCGTTCAAGATTCATAACAAG
ATTTGGGTTATTCCGGAACGTGATACCTTC
ACCAATCCGGAAGAAGGCGACTTAAACCCG
CCGCCAGAAGCCAAACAAGTGCCGGTGAGC
TACTATGATAGCACGTATCTTAGCACCGAT
AATGAAAAAGACAATTACCTGAAGGGCGTG
ACCAAGTTGTTCGAGCGCATCTACAGTACC
GACTTAGGCCGCATGTTGTTGACGAGCATC
GTTCGCGGTATCCCGTTCTGGGGCGGCTCG
ACCATTGATACCGAGTTGAAAGTCATTGAC
ACGAACTGTATCAATGTTATCCAACCGGAC
GGCAGTTATCGCAGCGAGGAGTTAAATTTG
GTCATCATCGGTCCAAGCGCAGATATTATT
CAGTTCGAATGCAAGAGCTTCGGCCATGAG GTCTTGAATTTGACGCGCAACGGTTACGGC
AGCACCCAATACATCCGCTTTAGCCCGGAT
TTCACCTTTGGCTTCGAGGAGAGCTTGGAG
GTGGACACCAACCCGCTGTTAGGTGCCGGC
AAATTCGCAACCGACCCGGCAGTGACGTTG
GCGCACGATTGATTCATGCGGGTCACCG
TTATACGGTATCGCGATCAATCCGAATCGC
GTCTTTAAAGTCAATACCAACGCGTACTAC
GAAATGAGCGGCTTAGAGGTTAGCTTTGAA
GAATTACGCACCTTCGGTGGCCACGACGCC
AAGTTCATCGACAGCCTGCAGGAAAATGAG
TTCCGCTTGTACTATTACAATAAATTCAAG
GACATCGCGAGCACCTTAAATAAAGCAAAG
AGCATTGTGGGCACCACCGCAAGCTTGCAG
TACATGAAGAACGTATTTAAGGAAAAATAT
TTGTTGTCGGAGGATACCAGCGGGAAATTC
AGCGTCGATAAGCTGAAATTCGACAAATTG
TATAAAATGCTGACCGAGATTTACACCGAG
GATAACTTCGTCAAGTTTTTTTAAGGTGTTA
AATCGTAAGACCTATTTAAACTTTGATAAA
GCGGTGTTTAAATTAATATCGTGCCGAAG
GTGAATTACACCATCTACGATGGTTTCAAT
TTACGCAACAGAATCTGGCGGCGGAATTTT
AATGGCCAAAACACCGAAATTAACAACATG
AACTTTACGAAGTTAAAGAATTTCACGGGC
TTATTCGAATTCTACAAGTTATTATGCGTG
CGCGGCATCATTACCAGCAAGGCAGGTGCG
GGCAAGTCCTTGGTTCCGCGTGGCAGCGCC
GGCGCCGGCGCGCTCAATGATCTGTGTATT
AAAGTCAATAACTGGGACCTGTTCTTCAGC
CCGAGCGAGGATAACTTTACCAACGACTTA
AACAAAGGCGAGGAGATCACGAGCGATACG
AACATCGAGGCGGCGGAGGAAATATTAGC
CTGGACCTCATTCAGCAGTACTATCTGACG
TTCAATTTTGACAATGAGCCGGAGAACATC
AGCATTGAAAATCTCAGCAGCGACATCATC
GGTCAGTTGGAACTGATGCCGAACATTGAA
CGCTTTCCGAACGGCAAAAAATATGAACTG
GACAAGTATACCATGTTCCATTACTTACGC
GCACAGGAATTTGAACACGGCAAGAGCCGC
ATTGCGCTGACCAATAGCGTTAACGAGGCC
TTGTTAAATCCGAGCCGTGTCTACACGTTC
TTCAGCAGCGATTATGTCAAAAAAGTGAAC
AAGGCGACCGAAGCGATGTTTTTGGGC
TGGGTCGAGCAATTGGTTTACGATTTTACC
GACGAAACCAGCGAGGTGAGCACGACCGAC
AAAATTGCAGATATCACCATCATCATTCCG
TACATCGGTCCGGCGCTCAATATCGGCAAT
ATGTTATACAAGGACGACTTTGTGGGCGCG
CTGATCTTTAGCGGCGCGGTTATCTTATTA
GAATTCATCCCGGAGATCGCAATCCCGGTC
TTGGGCACCTTTGCGTTGGTTGGTGAGCTATATC
GCGAATAAAGTGCTCACGGTCCAAACCATC
GATAACGCGCTCAGCAAGCGTAATGAGAAA
TGGGACGAGGTTTATAAGTATATCGTGACC
AACTGGTTAGCAAAGTCAATACGCAGATC
GATCTCATCCGCAAAAAAATGAAAGAAGCC
TTGGAAAATCAAGCGGAGGCAACCAAAGCC
ATCATTAATTACCAGTATAACCAATATACC
GAAGAAGAAAAAAACAATATCAACTTCAAT
ATCGATGATTTGAGCAGCAAACTGAACGAG
AGCATTAACAAAGCGATGATTAACATCAAC
AAGTTCTTGAATCAATGCAGCGTGAGCTAT
CTCATGAACAGCATGATCCCGTATGGCGTC
AAACGCTTGGAAGATTTTGACGCCAGCCTG
AAAGATGCGCTTCTCAAGTATATTTATGAC
AACCGCGGCACCCTCATTGGCCAGGTGGAC
CGCTTGAAGGATAAAGTGAACAATACGCTC
AGCACGGATATCCCGTTCCAGCTGAGCAAG
TACGTCGACAACCAGCGCTTACTGAGCACC
TTTACCGAGTATATCAAGAACATCATTAAT
ACCAGCATCCTCAACTTGCGCTATGAGAGC
AATCTCATCGACCTCAGCCGCTACGCC
AGCAAGATCAACATCGGCAGCAAGGTCAAT
TTCGACCCGATCGATAAGAATCAGATCCAA
TTGTTTAACCTGGAAAGCAGCAAGATCGAG
GTTATCTTGAAGAACGCGATTGTGTACAAC
AGCATGTACGAGAACTTTAGCACGAGCTTC TABLE 1-continued

| Sequences |
|---|
| TGGATTCGTATCCCGAAGTATTTCAATAGC |
| ATTAGCCTGAATAACGAATATACCATTATC |
| AACTGCATGGAAAATAATAGCGGCTGGAAG |
| GTGAGCTTAAATTACGGCGAGATCATTTGG |
| ACCTTACAGGATACCCAAGAAATCAAACAG |
| CGCGTCGTCTTTAAGTATAGCCAGATGATC |
| AACATCAGCGATTACATCAACCGCTGGATC |
| TTCGTGACCATCACCAATAATCGCTTGAAT |
| AATAGCAAGATTTACATCAATGGTCGCTTG |
| ATTGATCAAAAACCGATCAGCAATCTCGGT |
| AATATCCATGCCAGCAATAACATCATGTTT |
| AAGTTAGACGGTTGCCGCGATACCCACCGC |
| TATATCTGGATCAAGTATTTTAACTTATTT |
| GATAAGGAACTCAACGAAAAGGAAATTAAA |
| GACTTATATGACAATCAGAGCAATAGCGGC |
| ATCCTGAAGGATTTCTGGGGCGACTACCTG |
| CAGTACGATAAGCCGTACTATATGTTGAAC |
| TTGTATGACCCGAACAAATATGTCGATGTG |
| AACAATGTGGGTATTCGTGGCTATATGTAC |
| TTAAAGGGCCCGCGTGGTAGCGTGATGACC |
| ACGAATATTTACTTAAACAGCAGCTTATAC |
| CGCGGCACGAAGTTTATTATCAAGAAGTAT |
| GCCAGCGGCAACAAGGACAATATCGTCCGC |
| AACAACGACCGTGTGTATATTAACGTGGTG |
| GTGAAGAATAAAGAGTACCGCTTGGCCACG |
| AATGCGAGCCAGGCGGGCGTGGAAAAAATC |
| TTGAGCGCGTTGGAGATCCCGGACGTCGGC |
| AACCTCAGCCAGGTTGTGGTGATGAAGTCT |
| AAAAACGACCAGGGCATCACGAACAAGTGC |
| AAAATGAATTTGCAAGATAACAACGGCAAC |
| GACATCGGCTTTATTGGTTTTCACCAGTTC |
| AATAACATCGCCAAACTCGTGGCCAGCAAT |
| TGGTATAACCGCCAAATTGAACGCAGCAGC |
| CGCACGCTCGGCTGTAGCTGGGAGTTCATC |
| CCGGTGGACGATGGCTGGGGCGAGCGCCCG |
| CTCGGAGATCTGGTGCCACGCGGTTCCGCG |
| AATTCGAGCTCCGTCGACAAGCTTTGGAGC |
| CACCCGCAGTTCGAAAAATAA |
| |
| SEQ ID NO 11: PAS100 rBoNT/A (nucleic acid sequence) |
| ATGGGTAGCAGCCATCATCATCACCATCAT |
| GGTAGCCTGGTTCCGCGTAGCTCTTCTGCA |
| AGTCCGGCAGCACCGGCACCGGCTTCACCA |
| GCTGCACCAGCACCTAGCGCACCGGCAGCA |
| TCTCCAGCAGCCCCTGCACCGGCAAGCCCT |
| GCAGCTCCAGCACCGTCAGCACCAGCAGCA |
| AGCCCAGCTGCTCCTGCTCCAGCGAGCCCA |
| GCAGCGCCAGCTCCTAGTGCCCCTGCTGCC |
| TCTCCTGCTGCTCCGGCACCAGCAAGTCCT |
| GCTGCGCCTGCACCGAGTGCTCCGGCTGCT |
| AGTCCTGCCGCACCAGCTCCGGCTAGTCCA |
| GCTGCTCCAGCCCCTTCAGCCCCTGCAGCA |
| CCATTTGTGAACAAGCAGTTTAACTATAAG |
| GACCCGGTGAACGGTGTGGATATCGCGTAT |
| ATCAAAATCCCGAATGCGGGCCAGATGCAA |
| CCAGTCAAGGCGTTCAAGATTCATAACAAG |
| ATTTGGGTTATTCCGGAACGTGATACCTTC |
| ACCAATCCGGAAGAAGGCGATTTAAATCCG |
| CCGCCAGAAGCCAAACAAGTGCCGGTGAGC |
| TACTATGATAGCACGTATCTTAGCACCGAT |
| AATGAAAAAGACAATTACCTGAAGGGCGTG |
| ACCAAGTTGTTCGAGCGCATCTACAGTACC |
| GACTTAGGCCGCATGTTGTTGACGAGCATC |
| GTTCGCGGTATCCCGTTCTGGGGCGGCTCG |
| ACCATTGATACCGAGTTGAAAGTCATTGAC |
| ACGAACTGTATCAATGTTATCCAACCGGAC |
| GGCAGTTATCGCAGCGAGGAGTTAAATTTG |
| GTCATCATCGGTCCAAGCGCAGATATTATT |
| CAGTTCGAATGCAAGAGCTTCGGCCATGAG |
| GTCTTGAATTTGACGCGCAACGGTTACGGC |
| AGCACCCAATACATCCGCTTTAGCCCGGAT |
| TTCACCTTTGGCTTCGAGGAGAGCTTGGAG |
| GTGGACACCAACCCGCTGTTAGGTGCCGGC |
| AAATTCGCAACCGACCCGGCAGTGACGTTG |
| GCGCACGAATTGATTCATGCGGGTCACCGC |
| TTATACGGTATCGCGATCAATCCGAATCGC |
| GTCTTTAAAGTCAATACCAACGCGTACTAC |

TABLE 1-continued

| Sequences |
|---|
| GAAATGAGCGGCTTAGAGGTTAGCTTTGAA |
| GAATTACGCACCTTCGGTGGCCACGACGCC |
| AAGTTCATCGACAGCCTGCAGGAAAATGAG |
| TTCCGCTTGTACTATTACAATAAATTCAAG |
| GACATCGCGAGCACCTTAAATAAAGCAAAG |
| AGCATTGTGGGCACCACCGCAAGCTTGCAG |
| TACATGAAGAACGTATTTAAGGAAAAATAT |
| TTGTTGTCGGAGGATACCAGCGGGAAATTC |
| AGCGTCGATAAGCTGAAATTCGACAAATTG |
| TATAAAATGCTGACCGAGATTTACACCGAG |
| GATAACTTCGTCAAGTTTTTTAAGGTGTTA |
| AATCGTAAGACCTATTTAAACTTTGATAAA |
| GCGGTGTTTAAAATTAATATCGTGCCGAAG |
| GTGAATTACACCATCTACGATGGTTTCAAT |
| TTACGCAACACGAATCTGGCGGCGAATTTT |
| AATGGCCAAAACACCGAAATTAACAACATG |
| AACTTTACGAAGTTAAAGAATTTCACGGGC |
| TTATTCGAATTCTACAAGTTATTATGCGTG |
| CGCGGCATCATTACCAGCAAGGCAGGTGCG |
| GGCAAGTCCTTGGTTCCGCGTGGCAGCGCC |
| GGCGCCGGCGCGCTCAATGATCTGTGTATT |
| AAAGTCAATAACTGGGACCTGTTCTTCAGC |
| CCGAGCGAGGATAACTTTACCAACGACTTA |
| AACAAAGGCGAGGAGATCACGAGCGATACG |
| AACATCGAGGCGGCGGAGGAAAATATTAGC |
| CTGGACCTCATTCAGCAGTACTATCTGACG |
| TTCAATTTTGACAATGAGCCGGAGAACATC |
| AGCATTGAAAATCTCAGCAGCGACATCATC |
| GGTCAGTTGGAACTGATGCCGAACATTGAA |
| CGCTTTCCGAACGGCAAAAAATATGAACTG |
| GACAAGTATACCATGTTCCATTACTTACGC |
| GCACAGGAATTTGAGCACGGCAAGAGCCGC |
| ATTGCGCTGACCAATAGCGTTAACGAGGCC |
| TTGTTAAATCCGAGCCGTGTCTACACGTTC |
| TTCAGCAGCGATTATGTCAAAAAAGTGAAC |
| AAGGCGACCGAAGCCGCGATGTTTTTGGGC |
| TGGGTCGAGCAATTGGTTTACGATTTTACC |
| GACGAAACCAGCGAGGTGAGCACGACCGAC |
| AAAATTGCAGATATCACCATCATCATTCCG |
| TACATCGGTCCGGCGCTCAATATCGGCAAT |
| ATGTTATACAAGGACGACTTTGTGGGCGCG |
| CTGATCTTTAGCGGCGCGGTTATCTTATTA |
| GAATTCATCCCGGAGATCGCAATCCCGGTC |
| TTGGGCACCTTTGCGTTGGTGAGCTATATC |
| GCGAATAAAGTGCTCACGGTCCAAACCATC |
| GATAACGCGCTCAGCAAGCGTAATGAGAAA |
| TGGGACGAGGTTTATAAGTATATCGTGACC |
| AACTGGTTAGCAAAAGTCAATACGCAGATC |
| GATCTCATCCGCAAAAAAATGAAAGAAGCC |
| TTGGAAAATCAAGCGGAGGCAACCAAAGCC |
| ATCATTAATTACCAGTATAACCAATATACC |
| GAAGAAGAAAAAAACAATATCAACTTCAAT |
| ATCGATGATTTGAGCAGCAAACTGAACGAG |
| AGCATTAACAAAGCGATGATTAACATCAAC |
| AAGTTCTTGAATCAATGCAGCGTGAGCTAT |
| CTCATGAACAGCATGATCCCGTATGGCGTC |
| AAACGCTTGGAAGATTTTGACGCCAGCCTG |
| AAAGATGCGCTCCTCAAGTATATTTATGAC |
| AACCGCGGCACCCTCATTGGCCAGGTGGAC |
| CGCTTGAAGGATAAAGTGAACAATACGCTC |
| AGCACGGATATCCCGTTCCAGCTGAGCAAG |
| TACGTCGACAACCAGCGCTTACTGAGCACC |
| TTTACCGAGTATATCAAGAACATCATTAAT |
| ACCAGCATCCTCAACTTGCGCTATGAGAGC |
| AATCACCTGATCGACCTCAGCCGCTACGCC |
| AGCAAGATCAACATCGGCAGCAAGGTCAAT |
| TTCGACCCGATCGATAAGAATCAGATCCAA |
| TTGTTTAACCTGGAAAGCAGCAAGATCGAG |
| GTTATCTTGAAGAACGCGATTGTGTACAAC |
| AGCATGTACGAGAACTTTAGCACGAGCTTC |
| TGGATTCGTATCCCGAAGTATTTCAATAGC |
| ATTAGCCTGAATAACGAATATACCATTATC |
| AACTGCATGGAAAATAATAGCGGCTGGAAG |
| GTGAGCTTAAATTACGGCGAGATCATTTGG |
| ACCTTACAGGATACCCAAGAAATCAAACAG |
| CGCGTCGTCTTTAAGTATAGCCAGATGATC |
| AACATCAGCGATTACATCAACCGCTGGATC |
| TTCGTGACCATCACCAATAATCGCTTGAAT |

TABLE 1-continued

Sequences

AATAGCAAGATTTACATCAATGGTCGCTTG
ATTGATCAAAAACCGATCAGCAATCTCGGT
AATATCCATGCCAGCAATAACATCATGTTT
AAGTTAGACGGTTGCCGCGATACCCACCGC
TATATCTGGATCAAGTATTTTAACTTATTT
GATAAGGAACTCAACGAAAAGGAAATTAAA
GACTTATATGACAATCAGAGCAATAGCGGC
ATCCTGAAGGATTTCTGGGGCGACTACCTG
CAGTACGATAAGCCGTACTATATGTTGAAC
TTGTATGACCCGAACAAATATGTCGATGTG
AACAATGTGGGTATTCGTGGCTATATGTAC
TTAAAGGGCCCGCGTGGTAGCGTGATGACC
ACGAATATTTACTTAAACAGCAGCTTATAC
CGCGGCACGAAGTTTATTATCAAGAAGTAT
GCCAGCGGCAACAAGGACAATATCGTCCGC
AACAACGACCGTGTGTATATTAACGTGGTG

TABLE 1-continued

Sequences

GTGAAGAATAAAGAGTACCGCTTGGCCACG
AATGCGAGCCAGGCGGGCGTGGAAAAAATC
TTGAGCGCGTTGGAGATCCCGGACGTCGGC
AACCTCAGCCAGGTTGTGGTGATGAAGTCT
AAAAACGACCAGGGCATCACGAACAAGTGC
AAAATGAATTTGCAAGATAACAACGGCAAC
GACATCGGCTTTATTGGTTTTCACCAGTTC
AATAACATCGCCAAACTCGTGGCCAGCAAT
TGGTATAACCGCCAAATTGAACGCAGCAGC
CGCACGCTCGGCTGTAGCTGGGAGTTCATC
CCGGTGGACGATGGCTGGGGCGAGCGCCCG
CTCGGAGATCTGGTGCCACGCGGTTCCGCG
AATTCGAGCTCCGTCGACAAGCTTTGGAGC
CACCCGCAGTTCGAAAAATAA

---

The invention claimed is:

1. A recombinant clostridial neurotoxin comprising the amino acid sequence of SEQ ID NO: 8 or SEQ ID NO: 9.

2. A pharmaceutical composition comprising the recombinant clostridial neurotoxin of claim 1, and pharmaceutically acceptable solvents and/or excipients.

3. A method for the treatment of a cosmetic condition or disease requiring improved chemodenervation comprising administering the recombinant clostridia neurotoxin of claim 1, whereby administration manifests as longer lasting denervation relative to an identical clostridial neurotoxin without a protein segment consisting of at least 50 amino acid residues consisting of alanine, serine and proline residues.

* * * * *